(12) United States Patent
Zuluaga et al.

(10) Patent No.: US 9,125,610 B2
(45) Date of Patent: Sep. 8, 2015

(54) ORAL SCREENING DEVICE

(75) Inventors: Andrés Felipe Zuluaga, Houston, TX (US); Michael Jonathan Smith, Houston, TX (US)

(73) Assignee: REMICALM, LLC, Houston, TX (US)

( * ) Notice: Subject to any disclaimer, the term of this patent is extended or adjusted under 35 U.S.C. 154(b) by 561 days.

(21) Appl. No.: 13/506,669

(22) Filed: May 8, 2012

(65) Prior Publication Data

US 2012/0232406 A1 Sep. 13, 2012

Related U.S. Application Data

(63) Continuation of application No. 12/317,016, filed on Dec. 18, 2008, now abandoned.

(60) Provisional application No. 61/188,222, filed on Aug. 7, 2008, provisional application No. 61/199,466, filed on Nov. 17, 2008.

(51) Int. Cl.
*A61B 6/00* (2006.01)
*A61B 1/247* (2006.01)
*A61B 1/00* (2006.01)
(Continued)

(52) U.S. Cl.
CPC ............. *A61B 1/247* (2013.01); *A61B 1/00142* (2013.01); *A61B 1/043* (2013.01); *A61B 1/0623* (2013.01); *A61B 1/0646* (2013.01); *A61B 1/0676* (2013.01); *A61B 1/0684* (2013.01); *A61B 5/0071* (2013.01);
(Continued)

(58) Field of Classification Search
USPC ....................................... 600/476; 433/29–30
See application file for complete search history.

(56) References Cited

U.S. PATENT DOCUMENTS 5,139,421 A  8/1992 Verderber
5,457,611 A  10/1995 Verderber
(Continued)

FOREIGN PATENT DOCUMENTS

CN         1889894 A    12/2007
WO   WO 2004/103171 A2  12/2004

OTHER PUBLICATIONS

Ekaterina Svistun, et al. Optimal Visual Perception and Detection of Oral Cabity Neoplasia Reflectance and Fluorescence, 97 sheets, slide presentation by Spectroscopy Lab, University of Texas at Austin, TX.
(Continued)

*Primary Examiner* — Joel F Brutus
(74) *Attorney, Agent, or Firm* — Elizabeth R. Hall

(57) ABSTRACT

An oral cancer screening device 10 used for the detection of pre-cancerous and cancerous tissue has a power supply 100, an illumination source 200, a selector switch 300 that enables the activation of a specific wavelength of light from the illumination source 200, an electrical system 400 in communication with the selector switch 300 and the illumination source 200, a heat sink 500 in thermal communication with the illumination source, a filter or cover 600 to protect the illumination source, and a transparent sheath 700 for providing a sanitary shield for the device when it is brought into contact or close proximity with the patient oral cavity. The sheath may optionally have an angled mirror incorporated at a distal end of the sheath to provide the operator with a reflected image of the illuminated tissue 900. The operator will optionally utilize head mounted lenses 800 to assist the operator's visualization of the light from the illuminated oral cavity.

32 Claims, 18 Drawing Sheets

(51) Int. Cl.
*A61B 1/04* (2006.01)
*A61B 5/00* (2006.01)
*G01N 21/64* (2006.01)
*A61B 1/06* (2006.01)

(52) U.S. Cl.
CPC ............ *A61B 5/0084* (2013.01); *A61B 5/0088* (2013.01); *G01N 21/6447* (2013.01)

(56) References Cited

U.S. PATENT DOCUMENTS

| | | | |
|---|---|---|---|
| D370,063 S | 5/1996 | Spreckelmeier | |
| 6,069,689 A | 5/2000 | Zeng et al. | |
| 6,325,623 B1 | 12/2001 | Melnyk et al. | |
| 6,639,674 B2 | 10/2003 | Sokolov et al. | |
| 6,645,230 B2 | 11/2003 | Whitehurst | |
| 6,702,577 B2 | 3/2004 | Wong | |
| 6,962,690 B2 | 11/2005 | Kiefer et al. | |
| 7,287,981 B2 | 10/2007 | Hirsch | |
| 7,302,287 B2 | 11/2007 | Gandjbakhche et al. | |
| 7,365,844 B2 | 4/2008 | Richards-Kortum et al. | |
| 7,422,598 B2 | 9/2008 | Altshuler et al. | |
| 2002/0135694 A1 | 9/2002 | Williams | 348/375 |
| 2003/0076281 A1 | 4/2003 | Morgan et al. | 345/44 |
| 2004/0023184 A1 | 2/2004 | de Josselin de Jong et al. | |
| 2004/0218039 A1* | 11/2004 | Cooper | 348/66 |
| 2004/0254478 A1 | 12/2004 | de Josselin de Jong et al. | |
| 2005/0064371 A1 | 3/2005 | Soukos et al. | |
| 2005/0202363 A1 | 9/2005 | Osterwalder | |
| 2005/0234526 A1 | 10/2005 | Gilhuly et al. | |
| 2005/0282102 A1 | 12/2005 | Kert | 433/29 |
| 2006/0057535 A1 | 3/2006 | Tamburrino | |
| 2006/0057536 A1 | 3/2006 | Tamburrino et al. | 433/30 |
| 2006/0057537 A1 | 3/2006 | Tamburrino | |
| 2006/0071355 A1 | 4/2006 | DeFazio | 264/1.7 |
| 2006/0240375 A1 | 10/2006 | Soukos et al. | |
| 2007/0098233 A1 | 5/2007 | Chang et al. | |
| 2007/0121786 A1 | 5/2007 | Okawa et al. | 378/119 |
| 2007/0233209 A1 | 10/2007 | Whitehurst | |
| 2007/0259310 A1 | 11/2007 | Goodson et al. | |
| 2008/0008977 A1* | 1/2008 | Hirsch | 433/29 |
| 2009/0082695 A1 | 3/2009 | Whitehead | |

OTHER PUBLICATIONS

Kerr Corporation, Orascoptic product information, www.orascoptic.com, 2007.

LED Dental, Inc. Velscope, http://www.velscope.com/velscope/images.php, 2006.

* cited by examiner

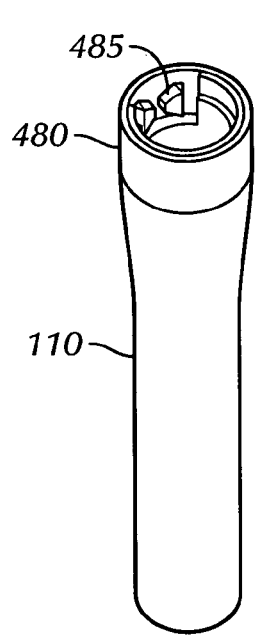
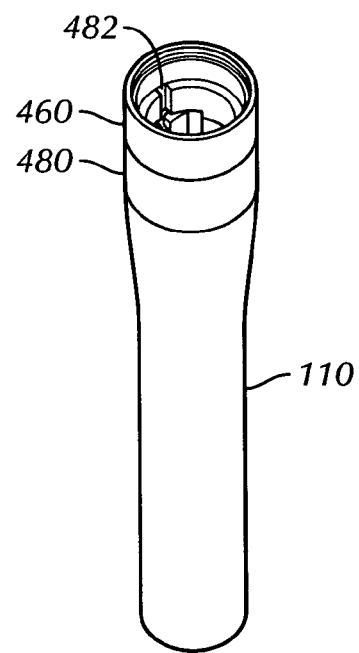
FIG. 20  FIG. 21
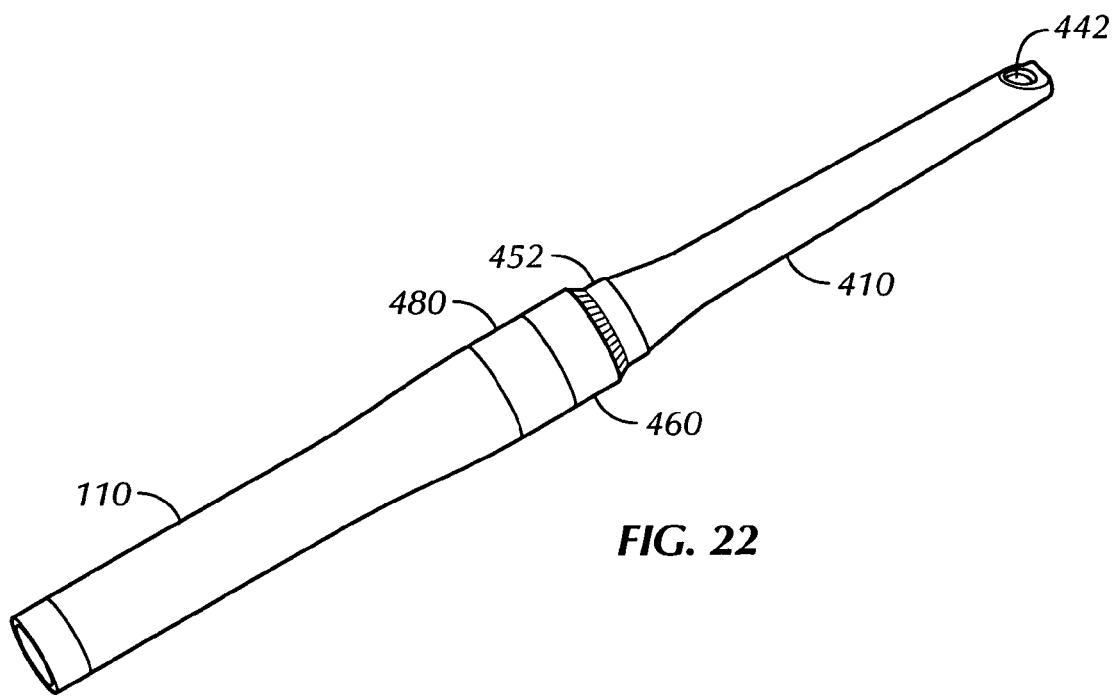
FIG. 22

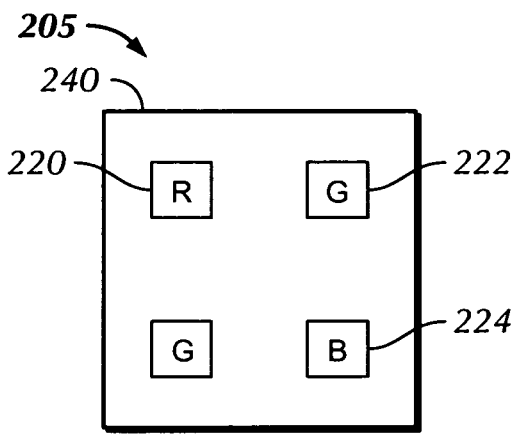
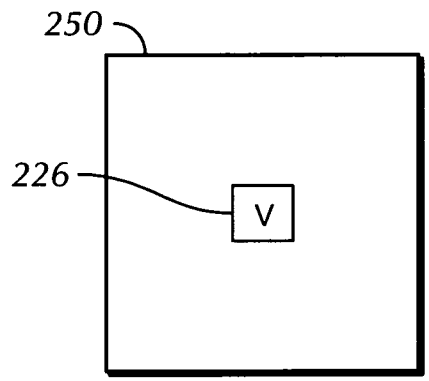
*FIG. 23A*   *FIG. 23B*
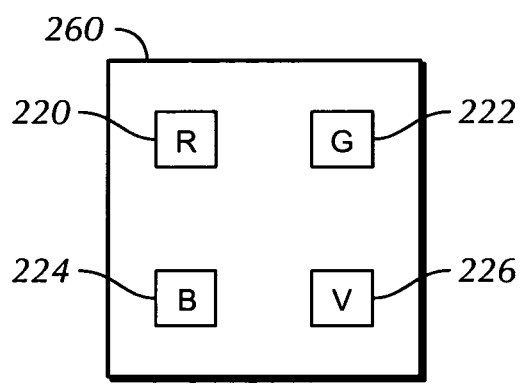
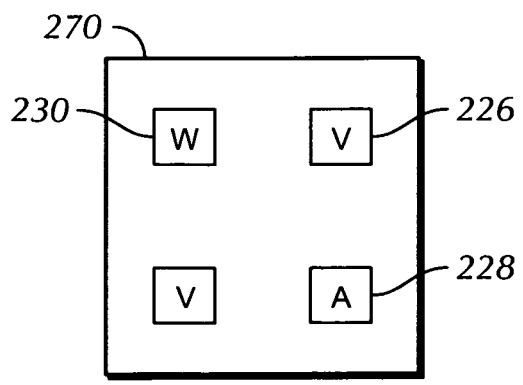
*FIG. 23C*   *FIG. 23D*

ORAL SCREENING DEVICE

CROSS-REFERENCE TO RELATED APPLICATION

The present application is a continuation of U.S. Ser. No. 12/317,016 filed Dec. 18, 2008, entitled "Oral Cancer Screening Device" by inventors Andres Felipe Zuluaga, et al., which claims the benefit under USC 119 of the filing date of provisional application Ser. No. 61/188,222 filed Aug. 7, 2008, and entitled "Apparatus for Optical Spectroscopic Identification of Cancer in Clinical Use" and provisional application Ser. No. 61/199,466 filed Nov. 17, 2008, and entitled "Oral Cancer Screening Device."

BACKGROUND OF THE INVENTION

1. Field of the Invention

The invention relates to a medical device for use in the identification of oral pre-cancerous and cancerous conditions. More particularly, the present invention relates to an oral cancer screening device having an illumination source, a selector switch to enable the selection of a light source having a specific wavelength, an LED or laser diode at a distal end of the device, and a filter, an optical mixing element or diffuser, a beam shaper or a cover to protect the LED or laser diode.

2. Description of the Related Art

A considerable number of oral cancerous and precancerous tissue changes are not visually apparent. The difficulty in detecting early stages of oral cancer means that oral cancer has one of the worst survival rates of all cancers. Yet whenever oral cancer is detected and treated early, patient survival is better than those of most cancers. Unfortunately, patient survival 5 years after diagnosis has remained poor, with little improvement over the last 30 years (<50%), mainly because most cases of oral cancer are detected late (at stages III and IV) in the disease process.

The American Dental Association estimates that 60% of the U.S. population has an annual dental exam. This fact provides the potential to include cancer screenings in annual dental exams so that oral cancer can be detected in its early stages. Unfortunately, published studies indicate that currently less than 15% of those who visit a dentist regularly report having had an oral cancer screening.

It is now commonplace for women to get an annual Papanicolaou (PAP) smear for cervical cancer screening or a mammogram to check for breast cancer. These screening efforts have been possible due to public awareness of the value of catching cancers in their earliest forms as well as effective technologies for conducting the examinations. If dental examinations included screening patients for oral cancer, the early detection of oral cancer would increase and lives would be saved.

Oral cancer is an ideal cancer to identify early by screening. It is frequently preceded by an identifiable pre-malignant lesion and the progression from dysplasia typically occurs over a period of years. However, before oral cancer screening will be incorporated into the normal dental examination, the dentist must have available effective and efficient technologies for conducting the examinations Accordingly, dentists need readily useable and economical tools for the early detection of cancerous changes in the mouth.

SUMMARY OF THE INVENTION

One embodiment of the invention provides an oral screening device for the detection of pre-cancerous and cancerous tissue. The screening device 10 has a power supply 100, an illumination source 200, a selector switch 300 that enables the activation of a specific wavelength of light from the illumination source 200, a microprocessor 400 in communication with the selector switch 300 and the illumination source 200, a heat sink 500 in thermal communication with the illumination source, a filter or cover 600 to protect the illumination source, and a transparent sheath 700 for providing a sanitary shield for the device when it is brought into contact or close proximity with the patient oral cavity. The sheath may optionally have an angled mirror incorporated at a distal end of the sheath to provide the operator with a reflected image of the illuminated tissue 900. The operator will optionally utilize head mounted lenses 800 to assist the operator's visualization of the light from the illuminated oral cavity. The filter or cover 600 may have optical mixing or beam shaping qualities.

Another embodiment of the invention is an oral screening device comprising: An oral screening device comprising: a power housing containing a power supply positioned at a first end of the device; an illumination source, wherein the illumination source includes a plurality of light emitters mounted on a second end of the device; a selector switch including a plurality of positions; an electrical system in communication with the illumination source and the selector switch positions, wherein a designated circuit in communication with one or more light emitters is selectably activated by each selector switch position; a heat sink in thermal communication with the light emitters; an electrical housing enclosing the electrical system, the illumination source, and the heat sink; and an operator head mounted lens.

Yet another embodiment of the invention is an oral device for screening for precancerous and cancerous tissue, the device comprising: a power housing containing a power supply positioned at a first end of the device; an illumination source, wherein the illumination source includes a plurality of light emitters mounted on a second end of the device; a selector switch including a plurality of positions, wherein each position activates a designated circuit in communication with one or more light emitters; an electrical system in communication with the illumination source and the selector switch positions, wherein the electrical system includes a microprocessor in communication with the selector switch; a heat sink in thermal communication with the light emitters; an electrical housing enclosing the electrical system, the illumination source, and the heat sink; a selectably attachable optically transparent sheath that covers the second end of the device when the sheath is attached to the device; and a protective cover for the illumination source positioned between the illumination source and the sheath.

Still yet another embodiment of the invention is an oral device for screening for precancerous and cancerous tissue, the device comprising: a power housing containing a power supply positioned at a first end of the device; an illumination source, wherein the illumination source includes a plurality of light units mounted on a second end of the device, each light unit mounting a light emitter; a selector switch including a plurality of positions, wherein each position activates a designated circuit in communication with one or more light emitters; an electrical system in communication with the illumination source and the selector switch positions, wherein the electrical system includes a microprocessor in communication with the selector switch; a heat sink in thermal communication with the light emitters; an electrical housing enclosing the electrical system, the illumination source, and the heat sink; a selectably attachable optically transparent sheath that covers the second end of the device when the sheath is attached to the device; a cover for at least one light emitter positioned between the illumination source and the sheath; and a viewing lens including a long pass filter.

A further embodiment of the invention is a method for screening a patient's oral cavity for precancerous and cancerous tissue, the method comprising the steps of: powering up an oral screening device having a power housing containing a power supply positioned at a first end of the device, an illumination source, wherein the illumination source includes a plurality of light emitters mounted on a second end of the device, a selector switch including a plurality of positions, wherein each position activates a designated circuit in communication with one or more light emitters, an electrical system in communication with the illumination source and the selector switch positions, wherein the electrical system includes a microprocessor in communication with the selector switch, a heat sink in thermal communication with the light emitters, an electrical housing enclosing the electrical system, the illumination source, and the heat sink, a selectably attachable optically transparent sheath that covers the second end of the device when the sheath is attached to the device, and a protective cover for the illumination source positioned between the illumination source and the sheath; turning the selector switch to a first position to activate one or more light emitters to produce white light; examining the oral cavity with white light; turning the selector switch to a second position to activate one or more light emitters to produce violet light; examining the oral cavity with violet light; and turning the selector switch to a third position to activate one or more light emitters to produce amber light; and examining the oral cavity with amber light.

The foregoing has outlined rather broadly several embodiments of the present invention in order that the detailed description of the invention that follows may be better understood. Additional features and advantages of the invention will be described hereinafter which form the subject of the claims of the invention. It should be appreciated by those skilled in the art that the conception and the specific embodiment disclosed might be readily utilized as a basis for modifying or redesigning the structures for carrying out the same purposes as the invention. It should be realized by those skilled in the art that such equivalent constructions do not depart from the spirit and scope of the invention as set forth in the appended claims.

BRIEF DESCRIPTION OF THE DRAWINGS

For a more complete understanding of the present invention, and the advantages thereof, reference is now made to the following descriptions taken in conjunction with the accompanying drawings, in which:

FIG. 20 shows an oblique view of the handle with the mode select ring in place.

FIG. 21 shows an oblique view of the handle with the mode select ring and the female ferrule in place.

FIG. 22 shows an oblique view of the assembled oral screening device having one light emission port.

FIGS. 23A-23D show various embodiments of light units and attached LED emitters.

DESCRIPTION OF THE PREFERRED EMBODIMENTS

Figure 1:
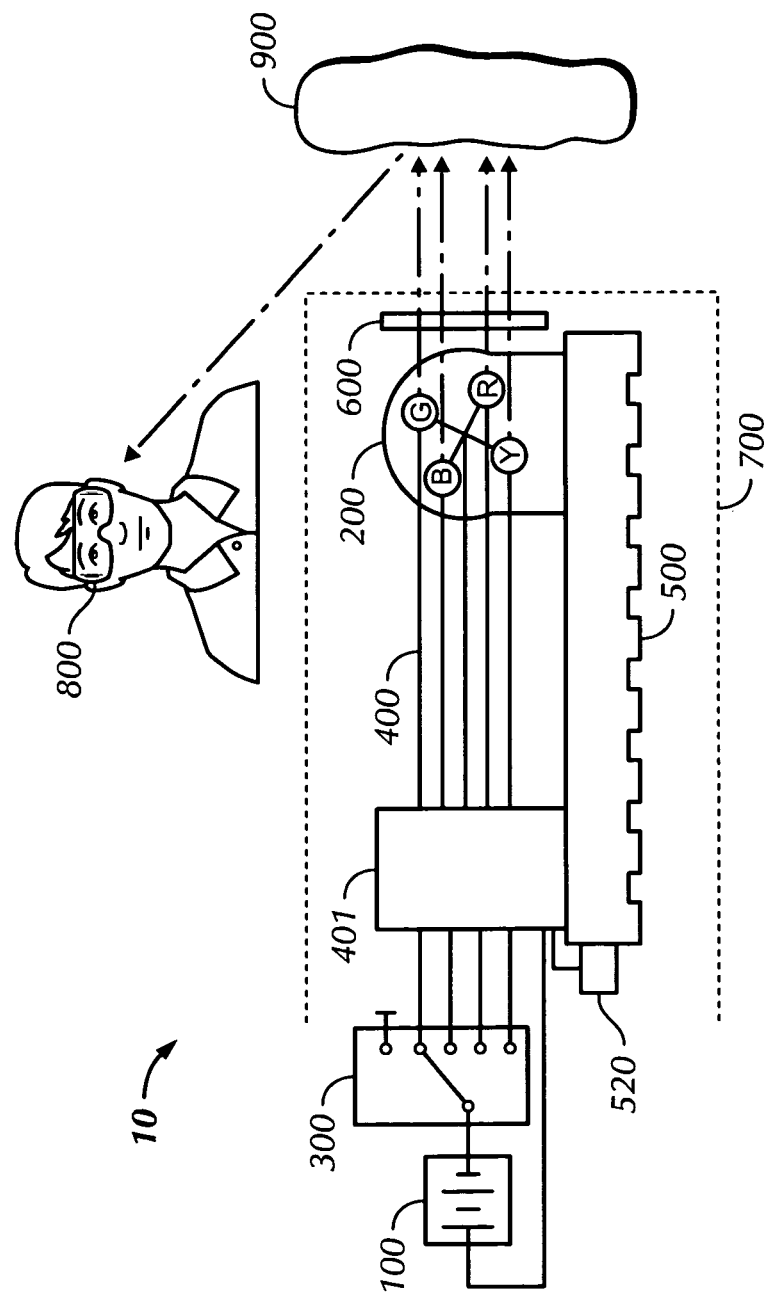
FIG. 1 is a schematic view illustrating the basic components of the oral screening device and their interrelationship.

The present invention relates to an oral cancer screening device used for the detection of pre-cancerous and cancerous tissue. As illustrated in FIG. 1, the screening device 10 has a power supply 100, an illumination source 200, a selector switch 300 that enables the activation of a specific wavelength of light from the illumination source 200, an electrical system 400 in communication with the selector switch 300 and the illumination source 200, a heat sink 500, a filter or cover 600 to protect the illumination source, and a transparent sheath 700 for providing a sanitary shield for the device when it is brought into contact or close proximity with the patient oral cavity. The sheath may optionally have an angled mirror incorporated at a distal end of the sheath to provide the operator with a reflected image of the illuminated tissue 900. In some cases, the operator can utilize head mounted lenses 800 to assist the operator's visualization of the light remitted from the illuminated oral cavity. The filter or cover 600 is defined herein to include an optical filter to filter the light passing through the filter, an optical mixing or beam shaping element to incorporate predetermined contributions from multiple light emitters, such as LEDs or laser diodes, onto a target.

These basic components may be implemented in a variety of embodiments and can be packaged in a number of configurations without departing from the scope of the invention as set forth in the claims. Although the components may be made of a variety of materials, generally the primary external structural components are made of aluminum, stainless steel, or structural plastic. Electrical conductors are typically made of copper or brass, while electrically insulating components are typically made of structural plastics. The sheath, a disposable sanitary protective cover, is made of a transparent optical grade plastic. The primary electronics for the unit are generally mounted on a conventional printed circuit board (either rigid or flexible), as is an element of the rotary illumination selection switch.

Figure 2:
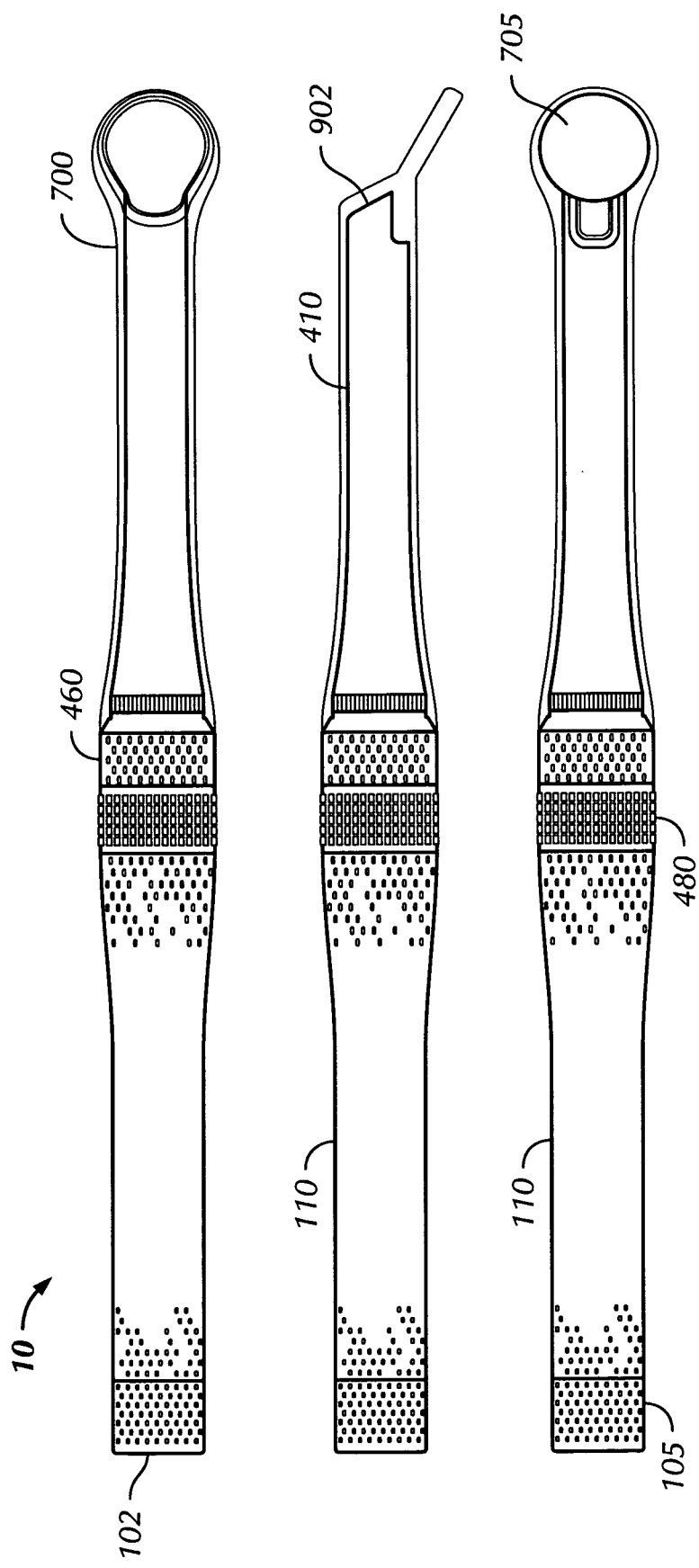
FIG. 2 shows the oral screening device in a back side view, a side view, and a front side view.

Referring to FIG. 2, the screening device 10 is shown sequentially from the top of the sheet in a back side view, a side view, and a front side view. Unless noted otherwise, the first end 102 of the device (also referred to as the proximal end) is shown to the left of the views and the second end 902 of the device (also referred to as the distal end) is shown to the right. For example, the handle or battery housing 110 of the screening device 10 is at the first end 102 of the device on the left hand side of FIG. 2. The externally visible parts of the screening device 10 are, from the first end 102, an on/off switch 105, a battery housing handle 110, a mode select ring 480, a female ferrule 460, an electrical housing 410, and a transparent disposable sanitary boot or sheath 700 which includes an offset mirror in its structure 705.

In order to ease description of the oral screening device, reference is made to vertical and horizontal planes of the device or part. Referring to FIG. 2, the upper view of the device is taken looking in the vertical plane, and the lower view also is taken looking in the vertical plane, but in the opposite direction. Thus the upper and lower views are normal to the horizontal plane. The first end of the device 102 is taken towards the left side of FIG. 1, while the second end 902 is taken towards the right side.

Power Supply and Battery Housing

Figure 3:
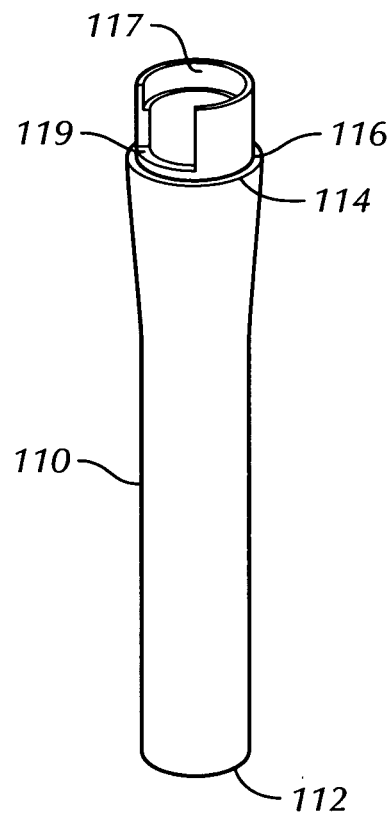
FIG. 3 shows the handle or battery housing of the oral screening device.

The battery housing or handle 110, shown in FIG. 3, is typically a tubular metal structure which serves to hold the power supply 100. The power supply 100 is preferably a rechargeable battery pack located in the battery housing handle 110. By way of example, the battery pack may be a stack of two AA batteries.

Adjacent the first end 102 of the screening device 10, the handle 110 has a transverse interior bulkhead that provides a first side to the battery compartment. An electrically conductive helical bias spring is mounted on an opposed second side of the transverse bulkhead to establish contact with the negative terminal of the battery pack. The spring is electrically isolated from the bulkhead, but is attached to an electrically conductive rivet which is externally insulated where it penetrates the bulkhead.

On the first side of the bulkhead, opposite to the second side mounting the spring, is located a short radially extending copper, stainless steel, or brass conductor strip electrically isolated from the bulkhead. This conductor strip is selectably electrically contacted by a switch contactor of the on/off switch 105 to apply or remove battery power from the oral screening device 10.

The first end 112 of the battery housing handle 110 has a female annular groove located in a short cylindrical tubular axial extension of the handle in the first side of the bulkhead. A nonconductive hollow cup-shaped end cap, at the extreme first end 102 of the device 10, is adapted so that it has a male annular ridge engagable with a snap fit with the female groove at the first end of the handle. Mounted interior to the cup is a second radially extending electrical contactor which has a contact button radially offset from the axis of the cup. The contact button of the second contactor can be rotationally selectably engaged and disengaged with the conductor strip mounted at the first side of the bulkhead of the handle 110. This second contactor extends radially outward and then parallel to the cup axis until it contacts the electrically conductive bulkhead of the handle 110. This arrangement provides one embodiment of an operator-selectable rotary on/off switch 105 for the battery power of the device.

The main bore of the battery housing handle 110 extends from the bulkhead to the second end 114. The main bore of the handle 110 is sized to provide a loose slip fit to the battery pack which is housed therein.

Near its second end 114, the tube of the battery housing handle 110 is enlarged. The second end 114 of the handle 110 has an exterior transverse shoulder 116 facing outward and a cylindrical extension 115 attached thereto. The bore of the cylindrical extension 115 has a short, slightly enlarged counterbore 117.

As seen in FIG. 3, a right circular arcuate segment of the cylindrical extension is cut away so that an arcuate transverse shoulder 119 is formed a short distance from the exterior transverse shoulder 116. This arcuate cutaway section permits the illumination selector switch 300 to operate in the resultant gap in the wall of the handle 110.

Selector Switch

Figure 4:
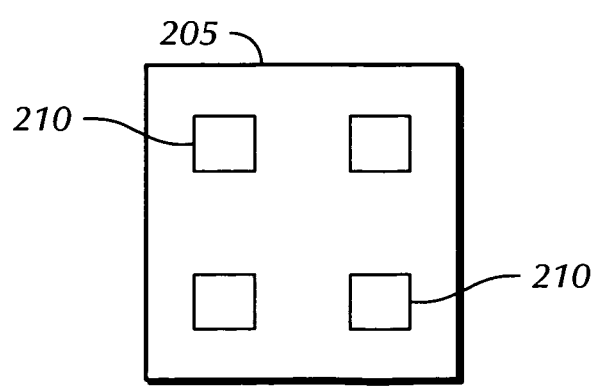
FIG. 4 is a schematic illustration of a light unit with four attached light emitters.

The illumination source 200 has a set of light emitters such that one or more of the emitters can be selectively activated to emit light of a specific wavelength band. As illustrated in FIG. 4, the illumination source 200 may be one or more light emitter units 205, wherein each unit 205 has one or more light emitters 210 attached thereto. Although, the units 205 include a variety of structure, they are hereinafter referred to as LED units 205. Similarly, although the light emitters 210 are preferably LEDs or laser diodes, they are hereinafter referred to as "LED emitters."

For example, the embodiment shown in FIG. 4 has four light emitters 210 attached to the light emitter unit 205. Each light emitter 210 positioned on a unit 205 may emit a different wavelength from each of the other light emitters 210 positioned on the unit 205, or more than one light emitter 210 may emit the same wavelength.

The unit 205 has its own internal routing circuitry installed during its fabrication at the supplier factory. For example, one or more of the light emitters 210 are wired on a particular circuit, such that the desired wavelength of light is produced whenever that particular circuit is activated.

The selector switch 300 has a number of positions and each position of the selector switch 300 is wired to activate a predetermined circuit designed to activate one or more LED emitters 210 to produce a particular wavelength of light, or combination of wavelengths. In operation, power is switched to a desired circuit by rotating the selector switch mode select ring 480 until the desired circuit is activated thereby activating the desired LED emitters 210 to produce the desired light bands. By separately and selectably powering selected subgroups of LED emitters 210, the operator can illuminate the oral cavity with one or more wavelength bands of light to differentiate between healthy and diseased tissue.

Preferably, each switch position is individually connected to a microprocessor which performs the actual switching of power to a designated circuit to power a particular desired combination of multiple individual LEDs used to provide light output of a selected wavelength of light.

Figure 5:
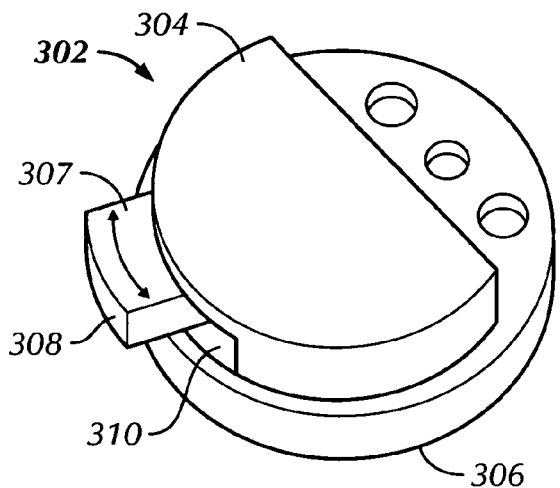
FIG. 5 is an oblique view of a first embodiment of the selector switch.

A first embodiment of the selector switch 302 having three switch positions is shown in FIG. 5. The switch core 304 is shown mounted onto a small circular secondary printed circuit board 306. The radially extending switch rotary contactor 307 is rotatable within a slot 310 of the main switch body, as seen in FIG. 5. The outer constant radius circumferential surface 308 of the switch rotary contactor 307 is electrically conductive and makes contact with the interior surface of the handle of the device. This same cylindrical conductive surface 308 is connected by a conductive copper trace to a switch contact button on a transverse face of the rotary contactor 307. Not shown in FIG. 5 are three output wires, with conduction through each wire being determined by the position of the rotary selector switch 300.

Figure 6:
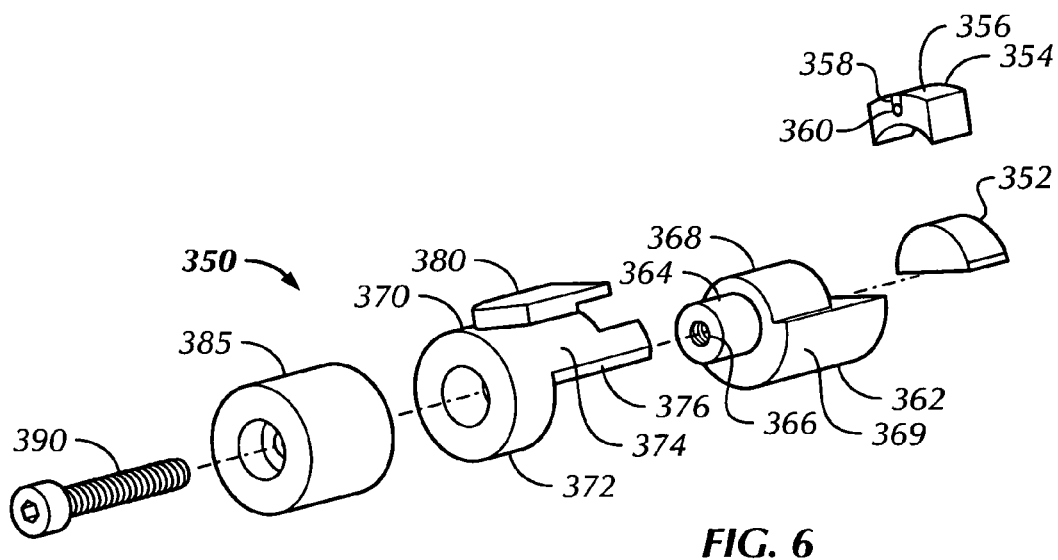
FIG. 6 is an exploded view of a second embodiment of the selector switch.

An exploded view of a second embodiment of the selector switch 350 is shown in FIG. 6. The components of selector switch 350 are functionally similar to the components of the selector switch 302. The switch core 352 is an axially relatively thin planar piece of plastic having a symmetrical rectangular profile on three sides and a circular arcuate profile on a fourth side, wherein the axis of the arc is perpendicular to the flat surface of the switch core. The center of the arcuate face is within the periphery of the body. The arcuate face is on the upper side of the switch core and adjoined by the relatively short vertical and parallel sides. The width of the horizontal bottom face is only slightly less than the diameter of the arcuate face.

Figure 7:
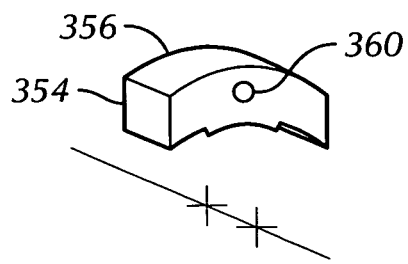
FIG. 7 shows the switching element.

The alternative switching element 354, illustrated in FIGS. 6 and 7, is a symmetrical thin planar arcuate segment having an inner diameter the same as the circular arcuate face of the switch core 352 and an outer diameter slightly more than that of the secondary printed circuit board (PCB) 306. The inner cylindrical face is slightly relieved radially outwardly on either side of the center section. The lateral sides are parallel to the part axis.

The outer cylindrical surface 356 of the switching element 354 is copper plated. A through hole parallel to the part axis is located on the radial midplane of symmetry of the switching element 354 approximately midway between the outer and inner cylindrical surfaces. On the first side of the switching element, a radial copper PCB trace 358 wider than the through hole extends inwardly just beyond the through hole. An electrically conductive rivet 360 is mounted in the through hole, with its end on the first side making electrical contact with the PCB trace and its second end serving as an electrical contact button.

The remainder of the parts shown in FIG. 6 are generally applicable to both the first 302 and second 350 embodiments of the switch 300, although the rotator hub 362 is axially shorter for the first switch embodiment 302.

Figure 8:
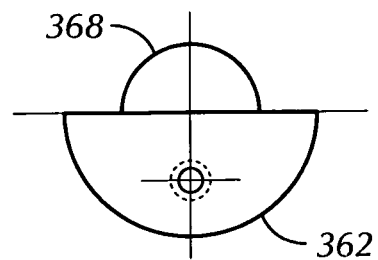
FIG. 8 shows a back side view of the rotator hub.

The aluminum rotator hub 362, seen in FIGS. 6 and 8, has on its first end a relatively short right circular cylindrical boss 364 having a first diameter and a drilled and tapped hole 366 on its centerline entering from the first side. Adjoining and integral with the second end of the boss 364 is a relatively short right first circular half-cylindrical segment 368 having an intermediate diameter. The plane containing the diameter of the first half-cylindrical segment 368 is horizontal, with the segment 368 lying above the plane. Below the first circular half-cylindrical segment 368 is a similar second half-cylindrical segment 369. The second half-cylindrical segment is longer than the first half-cylindrical segment 368 and has a larger diameter.

The two half-cylindrical segments 368 and 369 are integrally mated on their planes containing their diameters, with the second half-cylindrical segment 369 on the lower side of the rotator hub. Referring to FIG. 8, a drilled and tapped hole parallel to the part axis of symmetry is shown vertically offset downwardly from and parallel to that axis on the second end of the rotator hub 362.

An electrically nonconductive plastic rotator 370, seen in FIG. 6, has a right circular annular ring 372 located at its first end. The bore of the annular ring 372 is a rotational slip fit to the cylindrical boss 364 on the first end of the rotator hub 362, and the axial thickness of the annular ring 372 of the rotator 370 is the same as the axial length of the first cylindrical boss 364 of the rotator hub 362.

Projecting in the second direction from the second face of the annular ring 372 is a right circular cylindrical annular sleeve section 374 having an inner diameter equal to that of the first half cylindrical segment 368 of the rotator hub 362. The outer diameter of the projection annular sleeve section 374 is the same as the annular ring 372 on the first end of the rotator 370. The projection is equal in length to the first half cylindrical segment 368 of the rotator hub 362, and the projection is limited to only the region above the horizontal plane through the axis of the rotator 370.

On the second end of the projection annular sleeve section 374 are two parallel mirror image arms 376 having vertical inner faces which are parallel to the part axis and coplanar transverse second sides. The width between the vertical inner faces is the same as or only slightly more than the width between the vertical lateral faces of the switching element 354 so that the switching element can be engaged between those parallel faces. The outer diameter of the parallel arms is the same as that of the annular ring 372 at the first end of the rotator 370. Short symmetrical vertical external flats parallel to the part axis are slightly inset from the outer diameter of the rotator. The length of the parallel arms 376 is such that it is approximately equal to the thickness of the switch core 352.

On the upper side of the rotator 370 is an outwardly projecting integral torque transferal tab 380 which is symmetrical about the vertical midplane of the part. The torque transferal tab 380 has a rectangular profile when seen axially, but its first end tapers in width as it nears the first end of the part, while it has a transverse intermediate face coplanar with the second end face of the projected sleeve section 374 and a horizontal interior face parallel to the part axis lying at a larger radius from the axis than the outer cylindrical face of the part.

The switch core 252 is able to fit on top of the upwardly facing horizontal face of the rotator hub 362 and abut the transverse second face of the upper half cylindrical section 368 of the rotator hub. The switching element 354 in the assembly is laterally retained between the projecting arms 376 of the rotator 370 and radially constrained on its outward side by the inner horizontal face of the projection of the torque transfer tab 380 in the second direction. This in turn causes the inner cylindrical face of the switching element 354 to bear on the outer cylindrical face of the switch core 352. In order to ensure electrical contact between the outer cylindrical surface of the switching element 354 and the aluminum body of the electrical package housing 410, a small biasing leaf spring optionally may be installed on the cylindrical interface between the switch core 352 and the switching element 354.

The rotator 370 with its entrapped switching element 354 is rotatable about the cylindrical boss 364 on the first end of the rotator hub 362. The rotator 370 is retained in place by a metal screw 390 and an elastomeric annular right circular cylindrical insulating washer 385 having a counterbore on its first end to house the screw head. Tightening the screw causes the elastomeric insulating washer 385 to expand diametrically. This expansion is used to lock the switch parts inside the bore of the electrical package housing 410. The same screw 390 serves as an electrical contact for the positive terminal on the battery located in the bore of the handle 110 closest to the second end of the handle.

Printed Circuit Boards

Figure 9:
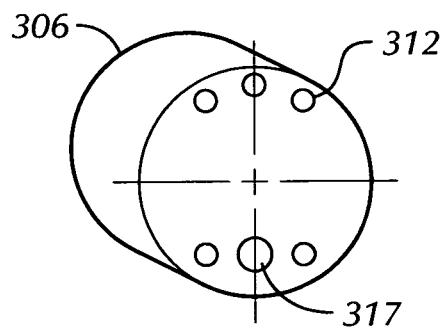
FIG. 9 shows an oblique view of the front of the secondary PCB.
Figure 10:
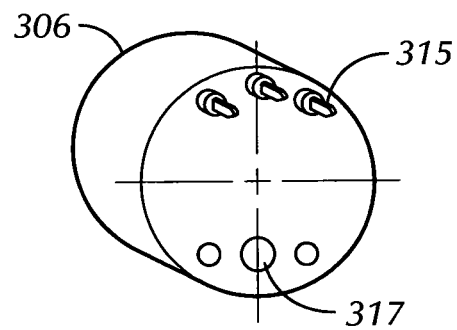
FIG. 10 shows an oblique view of the back of the secondary PCB.

In FIG. 9, the secondary printed circuit board (PCB) 306 is seen from its first side and in FIG. 10 the secondary printed circuit board 306 is seen from its second side. The secondary PCB 306 is a relatively thin right circular cylindrical disk having an electrically nonconductive body with six holes penetrating the body of the PCB parallel to the part axis of symmetry.

Figure 11:
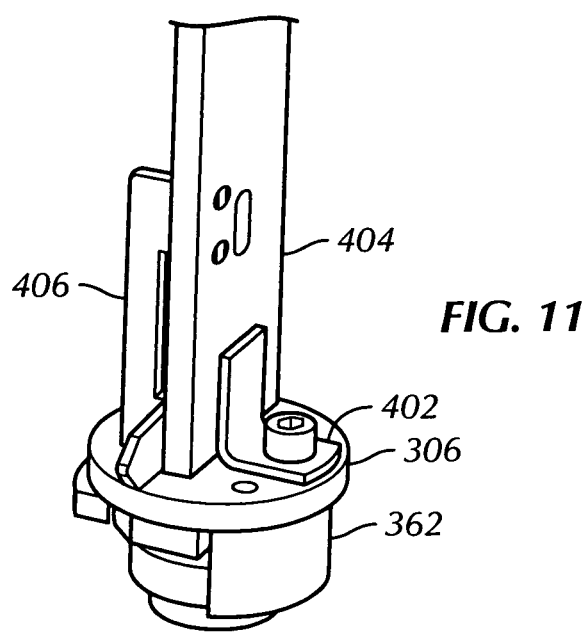
FIG. 11 shows the selector switch components attachment to the secondary PCB and the main PCB.

The three upper holes are coradial and equally spaced, symmetrically placed about the vertical plane through the part axis. These three upper holes are penetrated by electrically conductive rivets having contact buttons 312 on the first side of the secondary PCB 306 and attached connector terminal tabs 315 on the second side of the secondary PCB 306. On the lower half of the secondary PCB 306 equispaced from the horizontal midplane of the part and symmetrical about the vertical midplane are three more holes, with the central hole 317 of the set of three serving as a mounting hole for the electrically conductive screw 390 to attach both the secondary PCB 306 and the positive terminal 402 that is attached to the primary printed circuit (PCB) board 404 to the drilled and tapped hole 366 of the rotator hub 362. This attachment is shown in FIG. 11.

Figure 12:
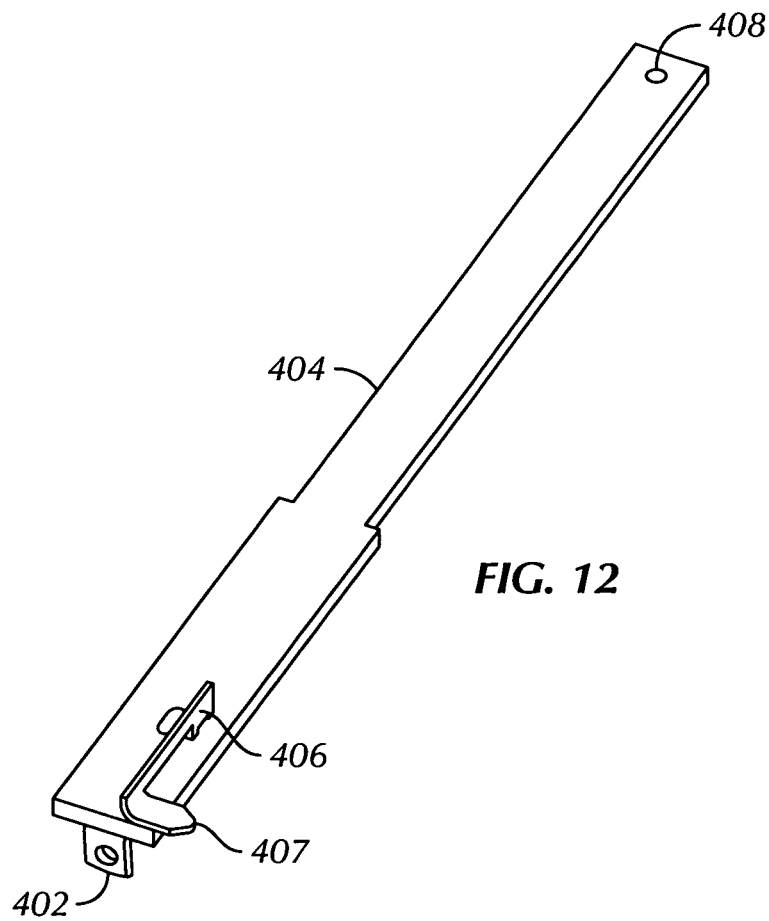
FIG. 12 shows and oblique view of the main PCB.

FIG. 12 shows the main PCB 404 in an oblique view. For simplicity, the electronic components which are used to regulate the power delivered to the LED unit 205 are not shown, but these items are well understood by those skilled in the art. The main PCB 404 is a planar piece of nonconductive plastic having an elongated rectangular first end and a cojoined elongated rectangular second end symmetrical with the first end. On a lower side, as seen in FIG. 12, the main PCB 404 has a short right angle bend conductive metal positive terminal 402. One leg of the angle, which has a width equal to about 40% of that of the first end of the main circuit board, is centrally placed on the lower side of the PCB 404 so that its right angle flange is flush with and transverse to the first end of the PCB. The positive terminal angle is soldered to through conductors penetrating the main PCB 404 to its upper side. The transverse flange of the positive terminal has a central through hole for mounting to the second end of the rotator hub 362 with an electrically conductive screw 390, as shown in FIG. 11.

A negative bus bar 406 is located on and mounted to the upper side of the main PCB 404 by engaging two prongs on its second end into corresponding holes in the main PCB 404 and then soldering the bus bar 406 to the PCB. The negative bus bar 406 is an elongate conductive metallic strip member which has the plane of its main body perpendicular to the upper surface of the main PCB 404, while the axis of the strip is parallel to the upper face of the main PCB. At its first end, a tab 407 is bent to project radially from the upper surface of the main PCB 404. The tab 407 projects beyond the lateral edge of the main PCB 404 and its tip serves as an electrical contact point to make contact with the aluminum electrical package housing 410 and the aluminum female ferrule 460. Because of the fixed anchorage of the negative bus bar 406 on its second end and the relatively long length of its unsupported strip, the negative bus bar 406 can flex in a radial direction relatively easily and without overstressing.

The main PCB 404 is provided with a pair of through holes 408 to facilitate its mounting by screws onto an aluminum heat sink bar 500 described below. All of the electronic components of the main PCB 404 are located on the upper side of the board. Electrical connector terminals are provided on the main PCB 404 for wires connecting to the three contactor terminals 312 on the secondary PCB 306. Additional electrical connector terminals are also provided on the main PCB 404 to connect to the lead wires supplying power to the LED unit 205.

Figure 13:
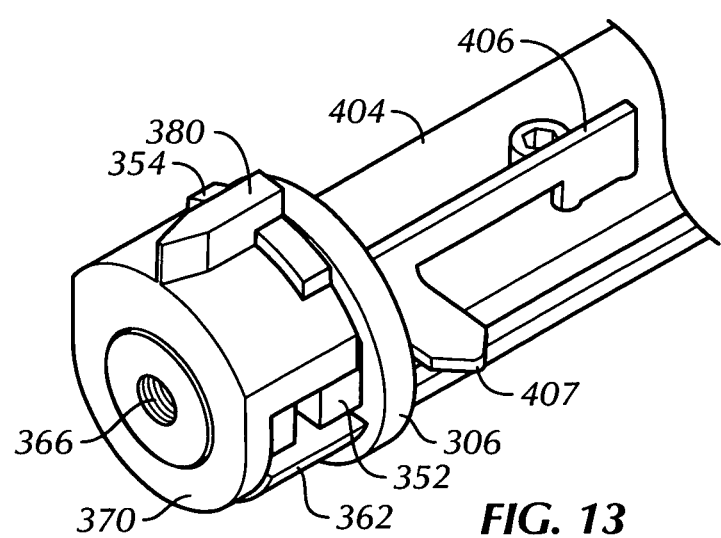
FIG. 13 shows the selector switch components attached to the secondary PCB and the main PCB.

The mounting of the electrical components of the rotary switch to the main and secondary PCBs is shown in FIG. 13. Electrical continuity for the positive portion of the circuit between the battery stack and the main PCB 404 is provided by the screw 390. The screw 390 passes through the elastomeric insulating washer 385 and the rotator 370, then it engages the threads on the second end of the rotator hub 362, the mounting hole 317 of the secondary PCB 306, and the positive terminal 402 of the main PCB 404.

Electrical continuity for the negative portion between the battery stack is provided through the battery spring and its mounting rivet to the on/off switch 105 on the first end of the handle 110 and then into the conductive aluminum handle 110. From the handle 110, the circuit passes through the conductive female ferrule 460 and the radially projecting negative bus bar contact point 407 to the main PCB 404. A branch connection passes through the female ferrule 460 into the outer cylindrical surface of the switching element 354 and then through the PCB trace and the through conductor 360 to the contact button of the rivet of the switching element 354.

When the mode select ring 480 and its rotationally engaged switching element 354 of the switch assembly are appropriately rotationally positioned, one of the branch negative circuits is completed by passing into the appropriate contact button of the through conductor 360 on the secondary PCB 315 and thence through the connecting jumper or fly wires to the appropriate branch of the main PCB 404.

Heat Sink

Figure 14:
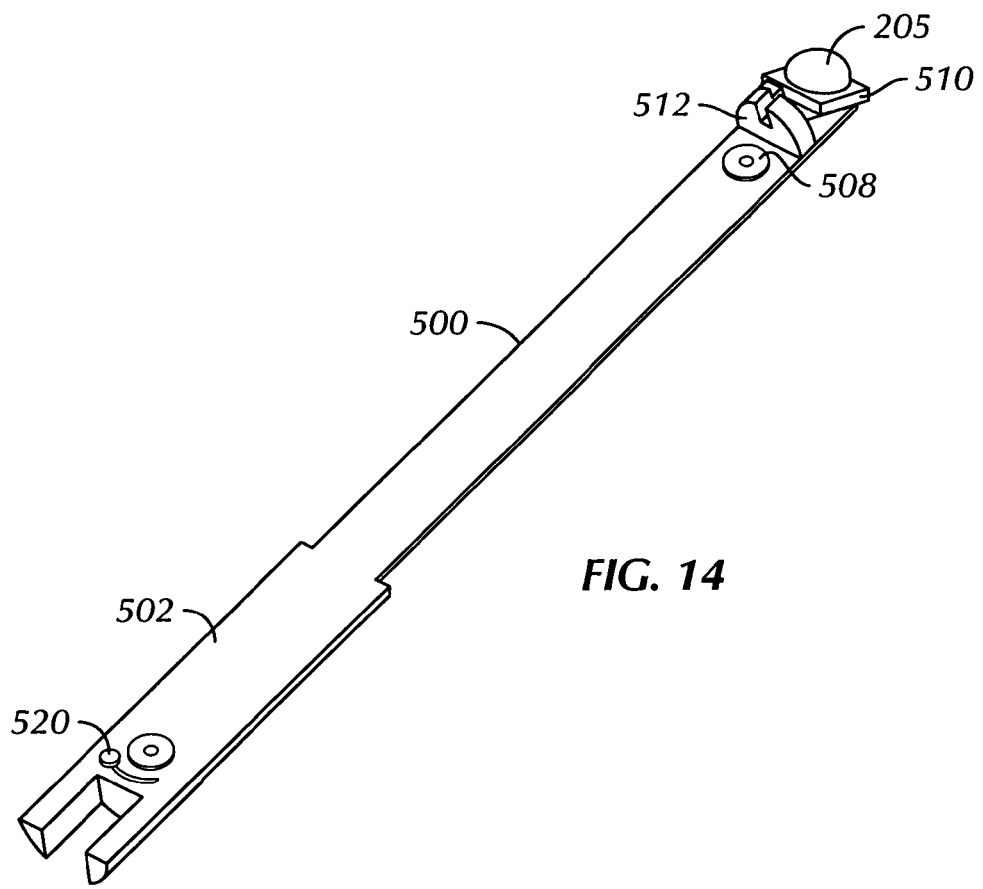
FIG. 14 shows an oblique view of the front side of the heat sink.
Figure 15:
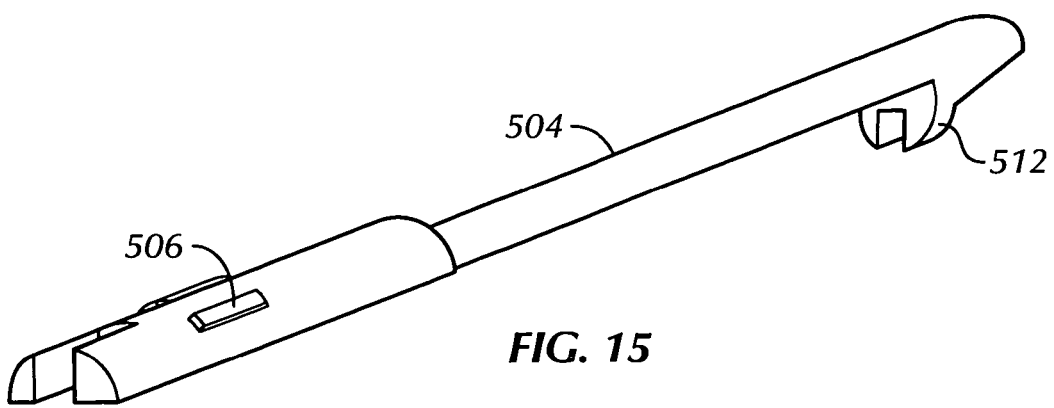
FIG. 15 shows an oblique view of the back side of the heat sink.

As seen in FIGS. 14 and 15, the machined aluminum heat sink 500 is an elongated bar having an upper substantially planar horizontal surface 502 parallel to the part axis and a lower opposed circularly arcuate obverse side 504. The obverse side 504 has one or more elongate circumferentially narrow protrusions 506 having equal radius cylindrical faces extending radially outwardly above its cylindrical surface 504. These protrusions 506 can be seen in FIG. 15. The function of the protrusions 506 is to make sufficient contact with the electrical package housing 410 so that heat can flow to the electrical package housing 410 where it can be dissipated.

As illustrated in FIG. 14, a thermostatic switch 520 is mounted by a thermally conductive adhesive in thermally intimate contact on the flat lateral surface 502 of the heat sink 500 near the notch on its first end. The thermostatic switch 520 opens and interrupts its internal circuit when the heat sink 500 exceeds a predetermined temperature. Two connecting leads extend from the thermostatic switch 520 so that their distal ends can be attached to the main PCB 404 and thence to the microprocessor 401 as schematically illustrated in FIG. 1.

The microprocessor 401 is programmed to cut off power to the illumination source 200 when the thermostatic switch 520 is opened in response to heat sink temperatures exceeding a preset limit. Alternatively, the thermostatic switch 520 may interrupt a common path in all circuits, therefore preventing the operation of the device if the temperature exceeds the preset limit.

The upper surface 502 of the heat sink is flat except for two drilled and tapped mounting bosses 508 for the main PCB 404, a transverse semicircular bulkhead 512 having a central radially extending notch for the wire leads of the LED unit 205, and a LED mounting surface 510. The LED mounting surface 510 is planar and is inclined relative to the horizontal surface of the heat sink 500, wherein the intersection of the horizontal surface 502 and the LED mounting surface 510 is a line lying in the horizontal plane and transverse to the long axis of the heat sink 500.

The first end of the heat sink has an elongated rectangular horizontal surface corresponding to that of the main PCB 404. Likewise, the second end of the heat sink has a second elongated rectangular horizontal surface corresponding to that of the main PCB, wherein the first and second rectangular surfaces of the heat sink are coplanar. A notch is provided at the first end of the heat sink so that there will be sufficient clearance for the positive terminal on the lower side of the main PCB at its first end. This clearance is to ensure electrical isolation of the positive terminal from the heat sink.

Figure 16:
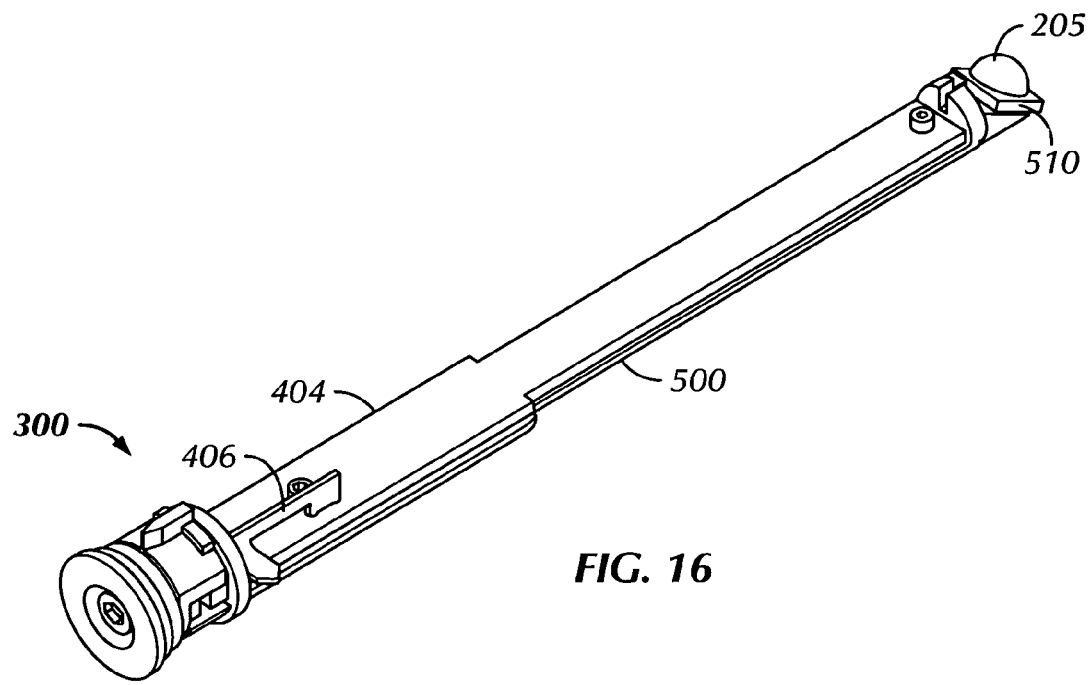
FIG. 16 shows an oblique view of the heat sink attached to the main PCB and the selector switch.

The mounting of the main PCB 404 to the heat sink 500 and the selector switch 300 is shown in FIG. 16.

Electrical Subassembly Housing

Figure 17:
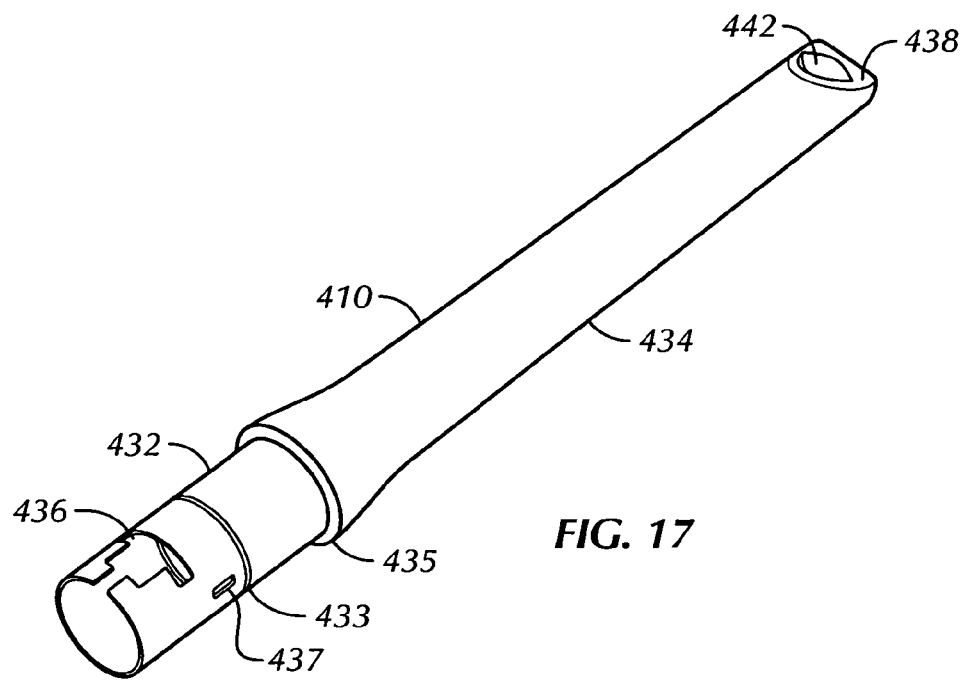
FIG. 17 shows an oblique view of the electrical system housing.

FIG. 17 shows the electrical package housing 410 in an oblique view from its first end. The electrical package housing is typically a turned tubular aluminum part with a thin wall tubular body at its first end. A first section 432 at the first end of the electrical package housing 410 has a constant outer diameter, with an annular male snap ring groove 433 located at approximately midlength of the first section 432.

The electrical package housing 410 has a shank 434 attached to the first section 432 at its first end. From its first end, the shank 434 has an external transverse shoulder 435 where it attaches to the first section 432, a short frustroconical transition to a slightly smaller diameter section, and a distal transverse second end. A flat 438, inclined to the axis of the electrical package housing 410, is machined in the shank 434 close to the distal end. The flat 438 converges toward the horizontal midplane of the electrical package housing 410 at the second end of the shaft.

The interior of the electrical package housing 410 has, from its first end, a first bore which extends almost to the snap ring groove 433 on the exterior surface, a short transition shoulder, a smaller second bore which extends to approximately the location of the external transverse shoulder 435, and then a long, smaller third bore which extends to almost the second end of the shank 434.

Figure 24:
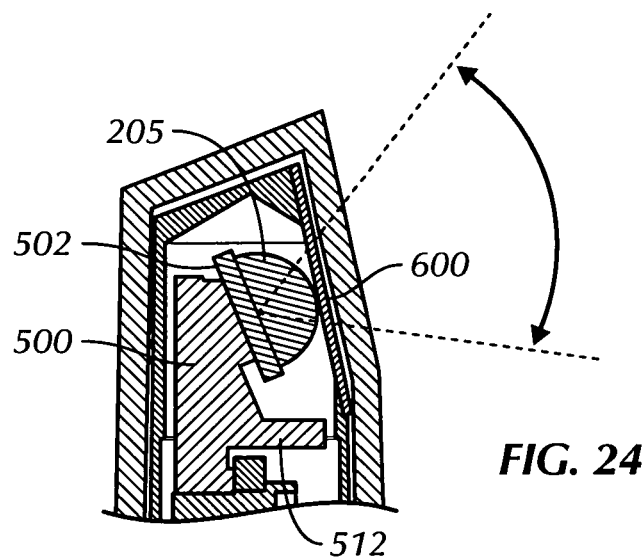
FIG. 24 shows a vertical cross-section of the distal end of the oral screening device having a single LED unit.

The first bore is a close slip fit to the elements of the rotary switch 300 assembly and the outer diameter of the secondary PCB 306. The second bore provides clearance to the components on the first end of the main PCB 404, while the third bore is a slip fit to the main PCB 404 and the heat sink 500. As can be seen in FIGS. 17 and 24, the machining of the distal external inclined flat 438 at the second end of the electrical package housing 410 penetrates into the interior cavity of the part to create an illumination emission port 442 or "window" for the light emitted from the light emitting unit 205.

The first section 432 of the electrical package housing 410 has a complex notch cut into its annular wall symmetrical about the vertical plane of the part and extending approximately 60% of the way from the first end to the male snap ring groove 433. This notch has its sides parallel to the vertical plane of the part. At the first end of the electrical package housing 410, the first short section of the notch is narrow, with clearance for the passage of the torque transfer tab 380 of the switch rotator 370. The middle section of the notch is wider that the first section. The middle section of the notch is sufficiently wide so that when the switch rotator 370 is moved to establish electrical contact with the off-center contactors 312 on the secondary PCB 306, the lateral sides of the torque transfer tab 380 will abut the lateral edges of the middle section of the notch. The third section of the notch has an axial length equal to slightly more than the thickness of the switching element and is made to be sufficiently wide circumferentially so that the switching element 354 can be moved to any of its switching positions.

A smaller circumferentially narrow notch 437 is provided in the electrical package housing 410 close to the male snap ring groove 433. As seen in FIG. 17, this narrow notch 437 provides a clearance hole to allow the protrusion of the contact tab 407 of the negative bus bar 406 on the main PCB 404 when the switch elements and the two PCBs are inserted into the electrical package housing, as shown in FIG. 18.

Figure 18:
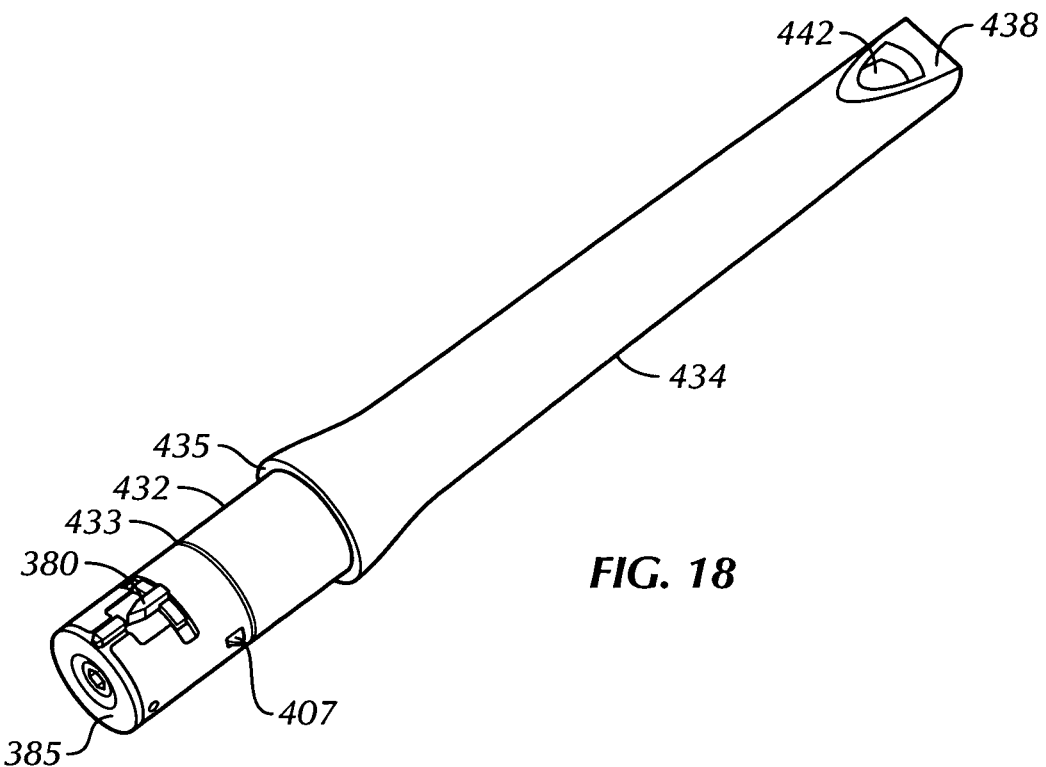
FIG. 18 shows an oblique view of the electrical system housing with the electrical system and the selector switch installed within.

As seen in FIG. 18, the insertion of the switch assembly and PCBs is done so that the contact point 407 of the negative bus bar 406 will protrude from the narrow notch 437, the switching element 354 will protrude from the third section 436 of the main notch, and the torque transfer tab 380 will protrude from the middle section of the main notch. The tightening of the screw 390 engaged through the elastomeric insulating washer 385 into the threads of the coaxial hole 366 on the first end of the rotator hub 362 causes the washer to radially expand to axially constrain the components of the rotary switch 300 and the PCBs to remain within the electrical package housing 410. When this is done, the LED unit 205 is aligned with the LED emission port 442 or window so that its light can project outwardly when the device of the present invention is activated.

Figure 19:
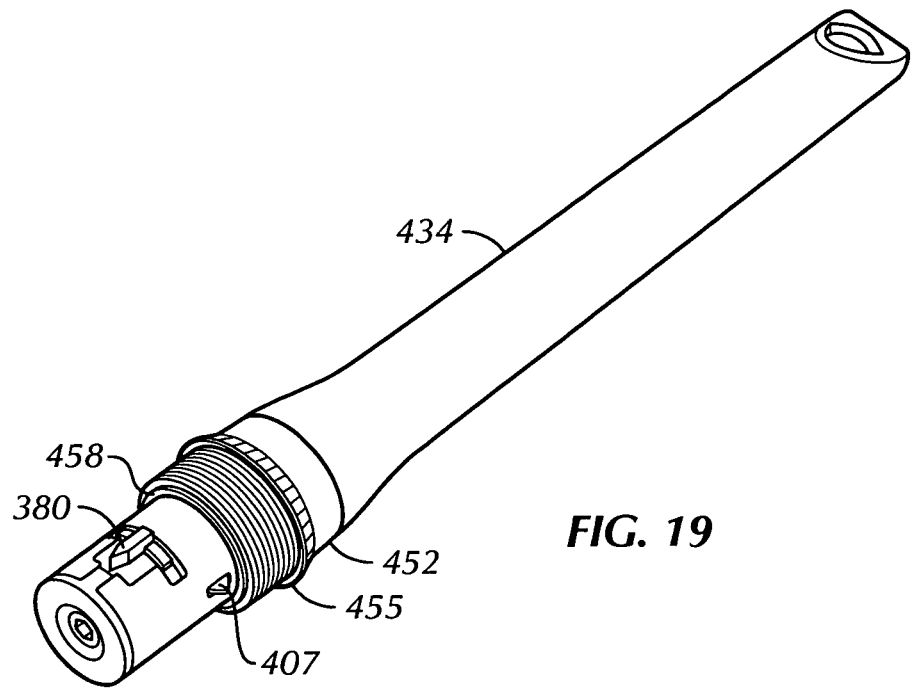
FIG. 19 shows electrical system housing of FIG. 18 with the lock nut in place.

An aluminum annular lock nut 452, shown in FIG. 19, has a bore which is a rotational slip fit with the exterior of the first section 432 of the electrical package housing 410. The axial length of the annular lock nut 452 is slightly less than the distance between the male snap ring groove 433 and the transverse shoulder 435 of the electrical package housing 410.

The lock nut 452 has a male thread on its exterior surface on its first end. The male thread extends approximately half of its axial length. At the second end of the male thread is an outwardly projecting transverse shoulder 455 facing the first end. Adjoining the transverse shoulder 455 on its second side is a short knurled frustroconical shoulder tapering inwardly in the second direction, followed by a constant diameter cylindrical surface. The diameter of this cylindrical surface is substantially the same as the maximum diameter of the external frustroconical section of the electrical package housing 410. The annular lock nut 452 is abutted against the intermediate transverse external shoulder 435 of the electrical package housing 410 and retained there by a male snap ring 458, as shown in FIG. 19.

An aluminum female threaded ferrule 460, shown in FIG. 21, is a relatively short annular element having at its second end the same outer diameter as the largest external diameter of the handle 110 and a female thread compatible with the male thread of the lock nut 452. At its first end, the female threaded ferrule 460 has a reduced diameter external cylindrical section which has a tight interference fit with the counterbore at the second end of the handle 110. The length of the reduced outer diameter section at the first end of the female ferrule is slightly longer than the depth of the counterbore at the second end of the handle 110. Internally at its first end, the female ferrule 460 has a transverse shoulder facing its second end and connecting the interior end of the female threaded section with a smaller through bore. A rectangular profile longitudinal slot 482 configured to freely pass the torque transfer tab 380 of the switch rotator 370 is cut parallel to the axis of the female ferrule 460 through the reduced bore section.

When the female ferrule 460 is slipped over the first end of the electrical package assembly where the threads of the female ferrule 460 abut but are not yet threadedly engaged with the male threads of the lock nut 452, the length of the female ferrule 460 is sufficiently short that it clears the torque transfer tab 380 of the rotator of the switch assembly. The female ferrule may have its larger exterior cylindrical surface knurled.

As seen in FIG. 20, a mode select ring 480 is an axially short annular ring having an outer diameter equal to the largest diameter of the upset portion of the exterior of the handle 110. The mode select ring 480 can be made either of aluminum, stainless steel, or a structural plastic. The diameter of the mode select ring 480, which may be knurled, is the same as the largest external diameter of the female ferrule 460. The inner cylindrical surface of the mode select ring 480 is a rotational slip fit to the reduced outer diameter section at the second end of the handle 110. Two symmetrically placed spaced apart radially inwardly projecting bosses 485 have parallel facing sides. The parallel facing sides are parallel to the part axis are located on the interior cylindrical section of the mode select ring 480. The gap between the two bosses is a close slip fit to the lateral sides of the torque transfer tab 380 of the switch rotator 370. The width of the bosses 485 is such that when the switch has its torque transfer tab 380 positioned between the two bosses 485, the mode select ring 480 can be rotated between extreme switch positions without the bosses 485 abutting the lateral sides of the notch at the second end of the handle 110. The length of the mode select ring 480 is slightly less than the reduced outer diameter section of the handle 110 at its second end. When the female ferrule 460 is pressed into the counterbore 117 at the second end of the handle 110 as shown in FIG. 2, the mode select ring 480 can still be rotated.

Attachment of the full electrical package, shown in FIG. 19, to the handle assembly, shown in FIG. 21, is effected by aligning the interior longitudinal notch 482 of the female ferrule 460 and space between the bosses 485 or slot of the mode select ring 480 so that the radially outwardly extending torque transfer tab 380 of the switch rotator 370 can be between them so that the tab 380 is only engaged with the slot of the mode select ring 480. At this point, the threads of the lock nut 452 can be threadedly engaged with those of the female ferrule 460 by rotating the handle 110 relative to the full electrical package. The result is the fully assembled oral screening device shown in FIG. 22.

Undoing this threaded connection between the full electrical package and the handle assembly provides access to the interior of the handle so that batteries can be readily changed. The positive terminal of the battery stack is biased into electrical contact with the head of the coaxially located screw 390 holding the elastomeric washer 385 of the switch assembly to the switch rotator hub 362.

Illumination Source

The illumination source 200 has a set of light emitters such that one or more of the emitters can be selectively activated to emit light of a specific wavelength band. As illustrated in FIG. 4, the illumination source 200 may be one or more light emitting units 205, wherein each unit 205 has one or more light emitters 210 attached thereto. Although, the units 205 include a variety of structures such as LED chips or laser diode chips, they are hereinafter referred to as LED units 205. Similarly, although the light emitters 210 are preferably LEDs or laser diodes, they are hereinafter referred to as "LED emitters."

For example, the embodiment shown in FIG. 4 has four light emitters 210 attached to the light emitter unit 205. Each light emitter 210 positioned on a unit 205 may emit a different wavelength from each of the other light emitters 210 positioned on the unit 205, or more than one light emitter 210 may emit the same wavelength.

FIG. 23 illustrates several examples of light emitting units (LED units) 205 that have one or more light emitters (LED emitters) 210 which are suitable for the present invention. In FIG. 23, R 220 indicates a LED emitter that produces red light, B 224 indicates a LED emitter that produces blue light, G 222 indicates a LED emitter that produces green light, W 230 indicates a LED emitter that produces white light, V 226 indicates a LED emitter that produces violet light, and A 228 indicates a LED emitter that produces amber light.

One embodiment of the LED unit 240, shown in FIG. 23A, has LED emitters suitable for emitting white, amber, and blue light. For the LED unit 240 shown in 23A, amber light is obtained when the red 220 and green 222 LED emitters are simultaneously activated. White light is generated when red 220, green 222, and blue 224 LED emitters are simultaneously activated. Blue light is generated when the blue 224 LED emitter is activated.

Violet light is particularly useful in exciting tissue blue/green autofluorescence for tissue diagnostics. The LED unit 250 shown in FIG. 23B has a single LED emitter that produces violet light. An LED unit such as the LED unit 250 may be used in conjunction with another LED unit 205 such as the LED unit 240 shown in FIG. 23A.

The LED unit 260, shown in FIG. 23C, has LED emitters suitable for emitting white, amber, blue, and violet light. For the LED unit 260, amber light is obtained when the red 220 and green 222 LED emitters are simultaneously activated. White light is generated when red 220, green 222, and blue 224 LED emitters are simultaneously activated. Blue light is generated when the blue 224 LED emitter is activated and violet light is generated when the violet 226 LED emitter is activated.

The LED unit 270, shown in FIG. 23D, has LED emitters suitable for emitting white, amber, and violet light. For the LED unit 270, amber light is obtained when the amber 228 LED emitter is activated. White light is generated when the white 230 LED emitter is activated and violet light is generated when the two violet 226 LED emitters are activated.

The LED unit 205 has its own internal routing circuitry installed during its fabrication at the supplier factory. One or more of the LED emitters 210 are wired on a particular circuit, such that the desired wavelength of light is produced whenever that particular circuit is activated. The selector switch 300 has a number of positions and each position of the selector switch 300 is wired to activate a particular circuit.

In one embodiment of the oral screening device a single LED unit 205 is mounted on the LED mounting surface 510 of the heat sink 500 as shown in FIG. 14. The assembled oral screening device with one LED unit 205 is illustrated in FIG. 22. As shown in FIG. 24, the LED unit 205 is aligned with the LED emission port 442 of the electrical package housing 410, so that the light emitted is directed to the tissue 900.

Figure 25A:
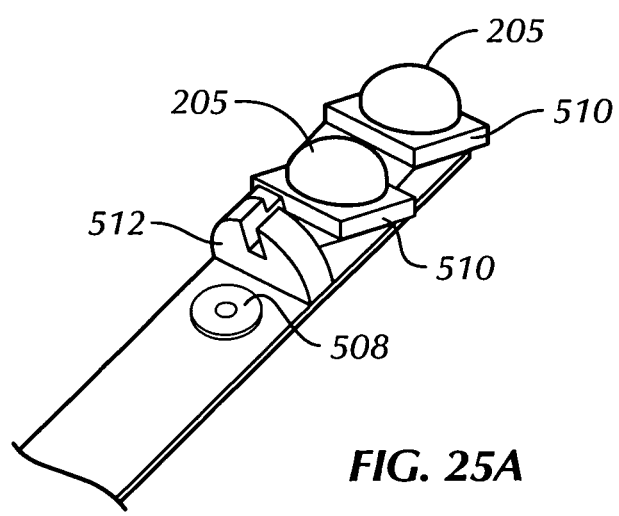
FIG. 25A shows an oblique view of the heat sink with two LED units attached.

For some applications, the oral screening device will preferably have more than one LED unit 205 to provide a wider choice of emitted light wavelengths available to the user. When two LED units 205 are used, the second end of the heat sink has its inclined distal surface for LED mounting surfaces 510 positioned differently as illustrated in FIG. 25A. For this situation, the distal tip of the heat sink has two separate but approximately parallel LED mounting surfaces inclined relative to the longitudinal axis of the part. These two mounting surfaces 510 are separated by an intermediate shoulder, so that light passage from the inwardly positioned first LED unit 205 will not pass through a window provided for the second LED unit 205.

Figure 25B:
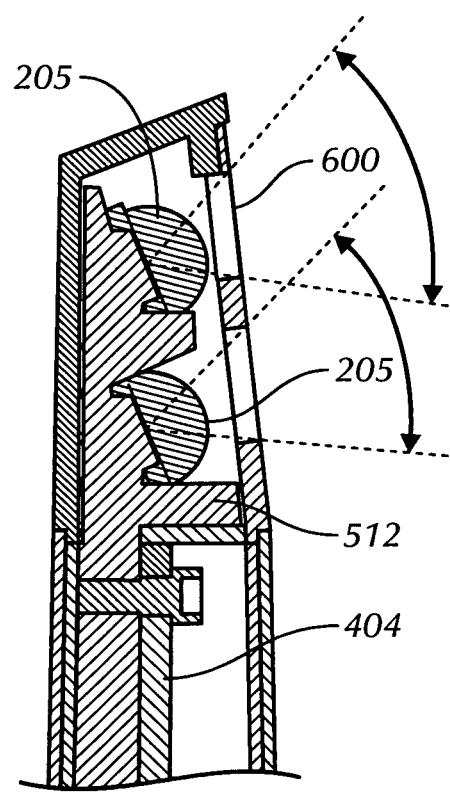
FIG. 25B shows a vertical cross-section of the distal end of the distal end of the oral screening device having two LED units.

An example of the oral screening device with two LED units 205 mounted on two mounting surfaces 510 of the heat sink is seen in FIG. 25A. The assembled oral screening device with two LED units 205 aligned with their respective LED emission ports 442 is illustrated in FIG. 25B. For this embodiment, the size of the LED emission ports may vary and added switch positions may be required in order to deliver the number of light emission wavelengths desired.

For the first embodiment having only one LED unit 205 the LED unit will preferably have multiple LED emitters, such as shown in FIGS. 23A, 23C, and 23D. For embodiments having two or more LED units, such as the embodiment shown in FIG. 25B, either one or both of the LED units 205 may have one or more LED emitters 210. A preferred embodiment would have one LED unit 240 (FIG. 23A) and one LED unit 250 (FIG. 3B).

Electrical System

The electrical system 400 is schematically illustrated in FIG. 1. The power 100 is turned on and the desired position on the selector switch 300 is selected by rotating the mode select ring 480 until the desired LED emitters 210 are activated. Each position of the selector switch 300 activates a particular channel of or through a microprocessor 401.

The microprocessor serves as a more capable switch, being able as a function off its programming to switch on power to a particular unique combination of multiple individual LED emitters 210 on a LED unit 205 in response to a specific signal transmitted over a specific input line designated by a specific position on the selector switch 300. When this switching by the microprocessor occurs, the elected set of LED emitters 210 is turned on with the desired light bandwidth is produced. The power supply for that group of LED emitters 210 on the LED unit 205 is selectably provided with negative polarity power which is appropriately conditioned and then transmitted over a dedicated wire connection to the LED unit 205.

Each LED unit 205 has its own internal routing circuitry installed during its fabrication at the supplier factory. One or more of the LED emitters 210 are wired on a particular circuit, such that the desired wavelength of light is produced whenever that particular circuit is activated.

Figure 26:
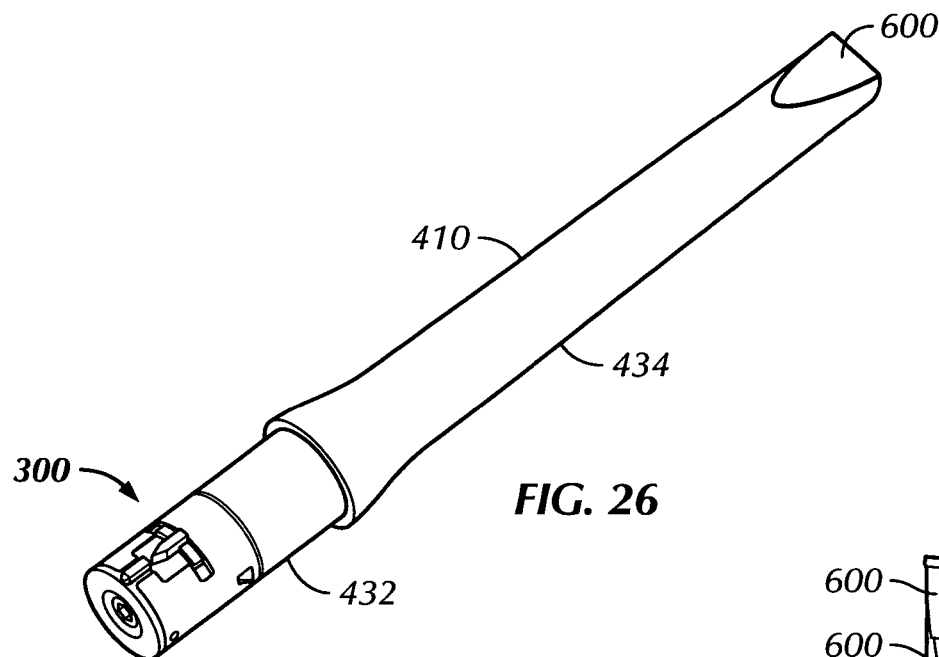
FIG. 26 shows an oblique view of the assembled electronics system of the oral screening device having a single LED unit.

For example, FIG. 26 schematically indicates how the switching provided by the microprocessor is used to selectably obtain particular light outputs from the LED unit 260, shown in FIG. 23C. The selector switch 300 is shown with three switch positions. Each position signals the activation of a designated circuit by the microprocessor 401 to activate specific LED emitters. More specifically, when switch position 1 is selected, the microprocessor 401 will activate red 220, green 222, and blue 224 LED emitters to produce white light; when switch position 2 is selected, the microprocessor 401 will activate red 220 and green 222 LED emitters to produce amber light; and when switch position 3 is selected, the microprocessor 401 will activate the violet 226 LED emitter to produce violet light.

The provision of multiple emitted combination spectra from the LED emitters 210 enhances the visual identification of diseased tissues due to differential reflectivity and autofluorescence from such tissues compared to healthy tissue.

Illumination Source Cover

The LED units 205 are provided with a cover 600 to protect the LED unit from environmental wear and tear. The cover 600 may be made of optically transparent glass or plastic, or it may be an optical filter to condition the emitted light. The cover may also serve the function of an optical mixing or beam shaping element to incorporate predetermined contributions from multiple light emitters 210, such as LEDs or laser diodes, onto the target illumination area. For example, lenses, prisms, diffusers or holographic masks may serve as optical mixers or beam shapers.

In FIGS. 24 and 26, a planar sheet of optically clear plastic is shown trimmed to fit and glued over the LED emission port 442 shown in FIG. 18. This piece of plastic can be fully transparent to the light wave length bands which will be emitted by the LED unit, or alternatively it can be used to provide filtering to the emitted light or predetermined mixing of the light emitted from the different LED emitters 210. In the case of the fully transparent plastic, the sheet serves as a protective guard for the LED unit.

Figure 27:
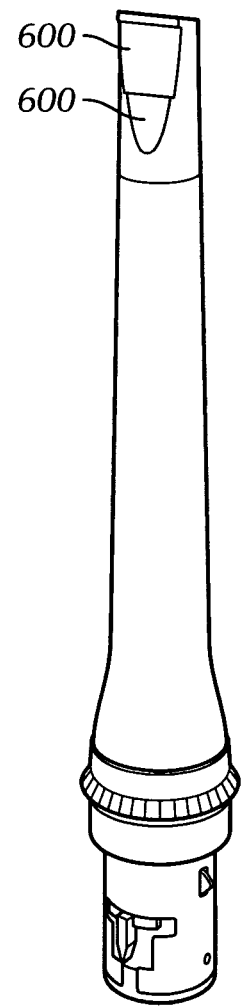
FIG. 27 shows an oblique view of the assembled electronics system of the oral screening device having two LED units.

FIG. 27 shows two similar covers 600 used for the two LED emission ports 442 when two LED units 205 are mounted in the oral screening device 10. Alternatively, a transparent optical grade plastic sub-sheath mounting an integral filter can be installed over the second end of the electrical package housing and the LED emission port 442. This arrangement offers, a potentially easier fabrication of the overall device while also providing additional protection for the device whenever the protective sheath is not in place covering the electrical package assembly.

Figure 28:
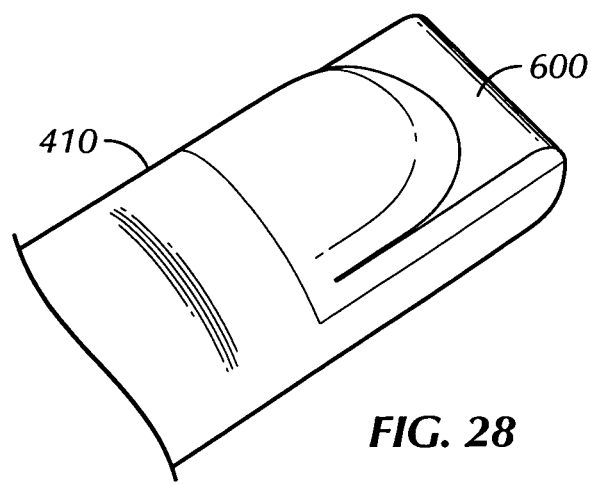
FIG. 28 shows an oblique view of the distal end of the oral screening device with a second embodiment of an illumination source cover.
Figure 29:
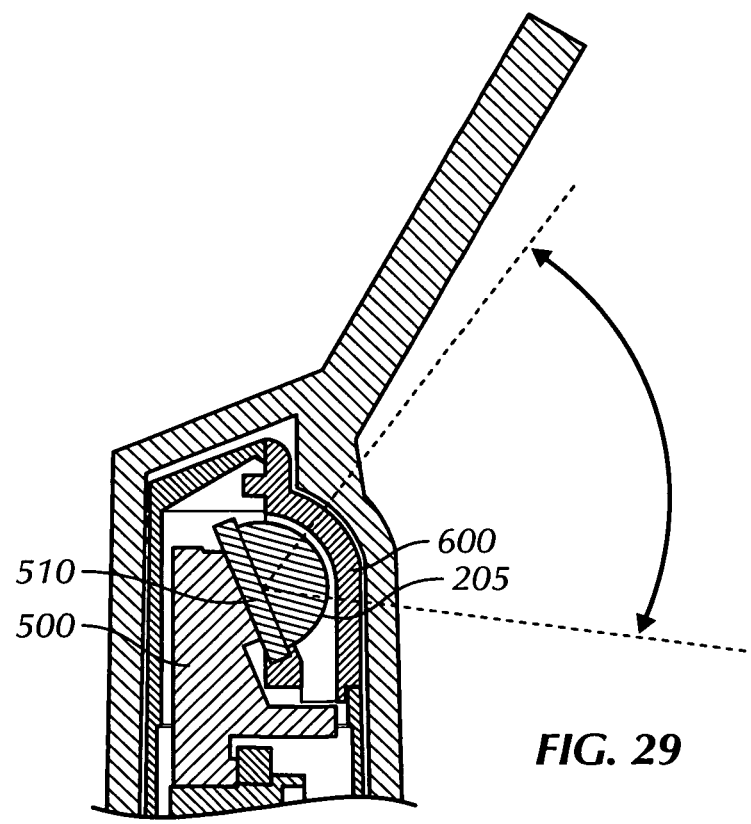
FIG. 29 shows a vertical cross-section of the distal end of the oral screening device having a single LED unit and a second embodiment of the illumination source cover with a sheath attached thereto.

FIGS. 28 and 29 show yet another embodiment of the cover 600, wherein the flat machined on the second end of the electrical package housing is made parallel to the part axis and moved transversely so that it lies either on or close to the part axis. The cut away portion of the flat results in the formation of a transverse shoulder facing in the second end of the electrical package housing. A molded window having a planar base sized to fit the flat on the second end of this electrical package housing is provided with a hollow half cylindrical lens extending approximately half of the length of the window and having a hollow quarter circular second end. The diameters of the half cylindrical lens portion and the quarter circular lens portion are the same inside and out so that there is a smooth transition between the two sections. Both diameters are equal to or slightly less than the diameter of the electrical package housing at its second end. The material should be optically clear, but can have filtering capabilities. If desired, alignment projections and other means can be provided to ease installation of the molded window onto the electrical package housing, as seen in the vertical midplane cross-sectional views of FIGS. 29 and 30.

Transparent Sheath

The sheath 700 is a disposable transparent sanitary shield that fits over the second or distal end 902 of the oral screening device 10. The use of a disposable sheath 700 during the screening of a patient's oral cavity for precancerous and/or cancerous tissue protects the screening device from coming into intimate contact with the patient. Thus, after screening the oral cavity of a first patient with the screening device 10, the first disposable sheath 700 can be properly disposed of as biological waste material. A new disposable sheath 700 can then be placed on the screening device 10 and used to perform an oral cavity screening of a second patient without having to disinfect the entire device.

The sheath 700 is molded from a strong optically clear grade of plastic with little or no autofluorescence when illuminated with violet light, such as polycarbonate, PTFE, FEP, or Plexiglas. The interior cavity of the sheath 700 is a loose slip fit over the distal end of the elongated body of the electrical subassembly housing 410. The sheath 700 typically has a snap fit onto and off of the device 10. This snap fit can be accomplished by the sheath 700 having a radial interference between the interior of the sheath and the knurled portion of the lock nut 452 on the electrical subassembly housing 410.

Figure 30A:
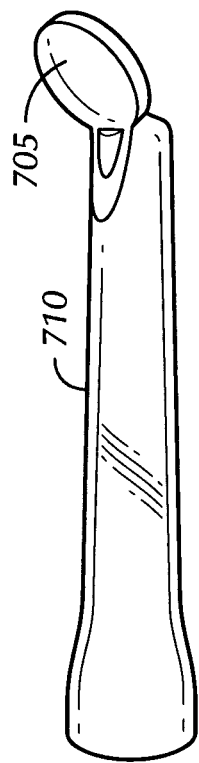
FIGS. 30A and 30B show two embodiments of a disposable sheath for protecting the distal end of the oral screening device.
Figure 30B:
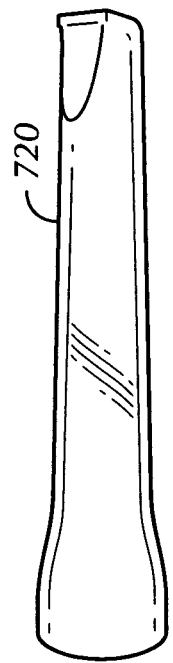

Two embodiments of the free standing sheath 700 are shown in FIG. 30. A first embodiment 710 has a distal end that mimics the shape of the distal end of the screening device 10. The second embodiment 720 supports an angled mirror 705 that eases the inspection of confined spaces by the operator.

Figure 31:
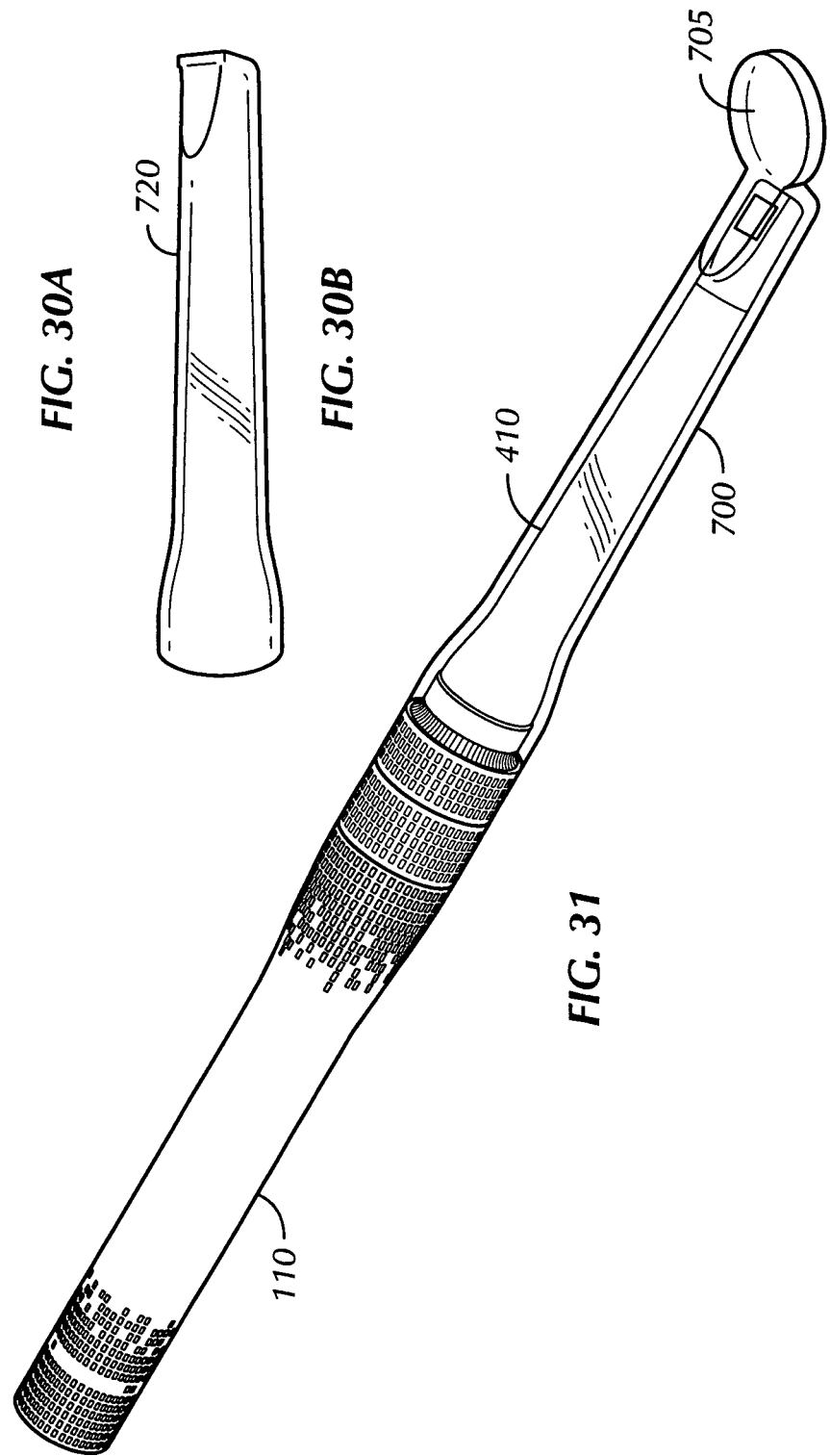
FIG. 31 shows an oblique view of a sheath covered oral screening device having a single LED unit.
Figure 32:
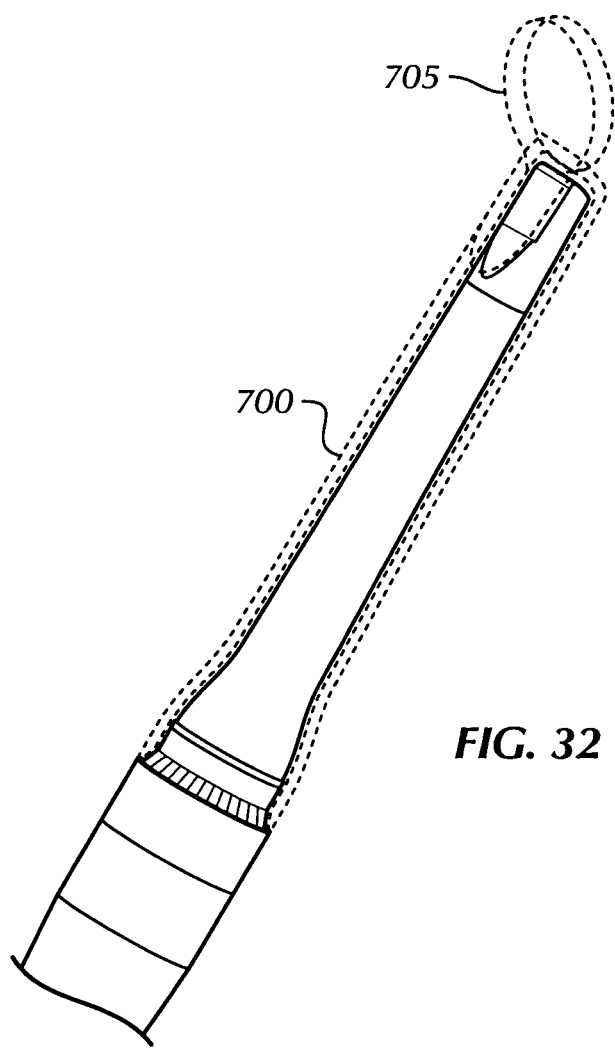
FIG. 32 shows an oblique view of a sheath covered oral screening device having two LED units.

FIG. 31 shows the sheath 700 in its installed position over the oral screening device 10 shown in FIG. 22 that has one LED unit. Similarly, FIG. 32 shows the sheath 700 installed over the oral screening device shown in FIG. 27 that has two LED units.

Figure 33:
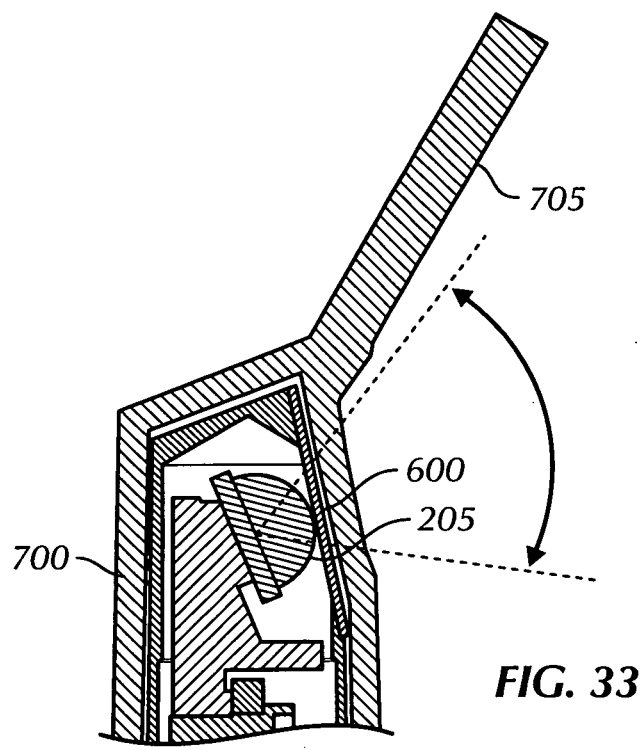
FIG. 33 shows a vertical cross-section of the distal end of the oral screening device having a single LED unit with a first embodiment of the illumination source cover with a sheath attached thereto.

FIG. 33 shows a vertical centerline cross-sectional view of the outer tip of the screening device 10 and indicates the optical path as the emission arc for the LED unit. The portion of the sheath 700 which overlies the LED emission port and the LED unit cover 600 has a uniform thickness, so that it is optically plano-plano. The size of the plano-plano portion of the sheath 700 is as large as necessary to ensure that the emitted light from the LED unit can be passed therethrough undistorted.

The mirror 705 is typically a planar thin circular disk which is mounted on the distal tip of the sheath 700 inclined to the sheath axis and in a position offset to the side of the plano-plano portion of the sheath. The disk is provided with a reflective surface on its side adjacent where the plano-plano portion of the sheath 700 is located by gluing a glass mirror onto the surface of the disk or by sputtering or plating the disk with a metallic reflective surface. The angle of the mirror face relative to the sheath axis and its axial position is constrained to avoid impingement of unreflected light emitted by the LED unit.

If two LED units 205 are mounted on the heat sink and used in the oral screening device 10, then the length of the plano-plano portion of the sheath would be increased in order to accommodate both LED units.

Operator Head Mounted Lenses

The operator may selectably use a set of head mounted lenses. The lenses serve to protect the eyes of the operator, although the lenses may also serve to filter the reflected or autofluorescent light emanating from the tissue 900 in response to light shone on the tissue 900 by the oral screening device 10. The lenses may be a uniform material, or the lenses may be split lenses, having one or more optical elements, For example, one embodiment of the head mounted lenses illustrated in FIG. 34 has two sections of different optical properties.

When autofluorescence is to be detected from the tissue 900, it is highly desirable to filter the fluoresced emission from the tissue specimen illuminated by the illumination source. For example, violet light (405 nm±25 nm) excites blue/green tissue autofluorescence. Thus, if violet light is used to excite the autofluorescence of the tissue, it is useful to use a filter for blue and green emissions to separate the autofluorescence from other extraneous light. Thus, a longpass filter that passes light having a wavelength of 435 nm and greater may be incorporated into the head mounted lenses 800. The head mounted lenses are typically designed to allow the transmission of 400-700 nm light, or preferably 430-580 nm light.

Figure 34:
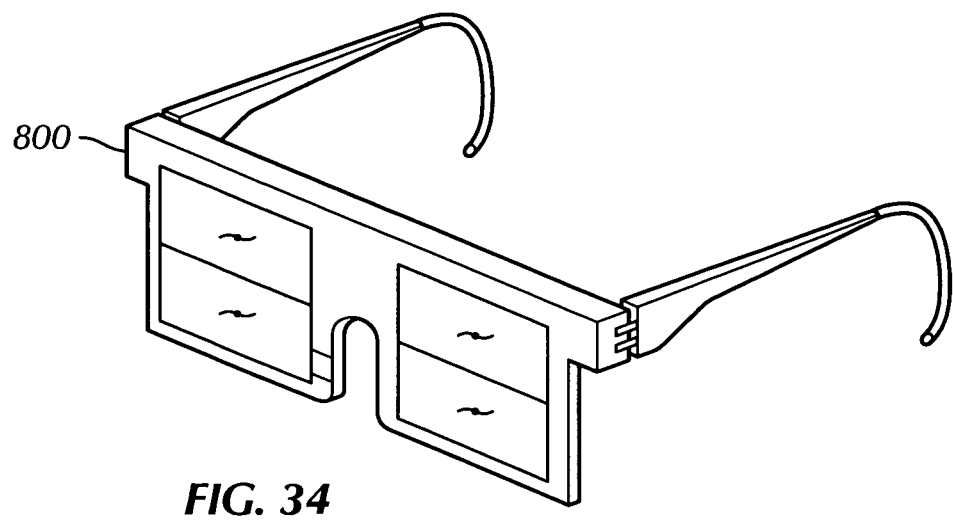
FIG. 34 shows an oblique view of the head mounted lenses.

The embodiment of the head mounted lenses shown in FIG. 34 has clear glass or plastic on the upper half of the lenses and a longpass filter on the bottom half of the lenses. By suitably tilting the head of the operator in a manner similar to that employed by users of bifocals, the operator can selectably filter the image which he is viewing. Thus, when white light or amber light is used to view the oral cavity, the operator views the reflectance emanating from the tissue through the upper half of the lenses; but when the fluorescent excitation is provided by violet light, the operator views the fluorescing tissue through the filtering lower half of the glasses.

Operation of the Screening Device

The dental screening device 10 is a battery operated, hand-held multispectral oral examination light used in conventional and specialized oral examinations. Accessories include light filtering glasses and single use, disposable protective sheaths with mirrors.

The dental screening device 10 uses white, violet and amber lights to screen the oral tissue in distinct and unique ways. Specifically, biochemical changes are monitored with fluorescence, while morphological changes are monitored with reflectance. The oral screening device 10 is intended to be used by qualified health-care providers to enhance the identification and visualization of oral mucosal abnormalities that may not be apparent or visible to the naked eye, such as oral cancer or premalignant dysplasia Head mounted lenses 800 contain reusable polarized filtered lenses worn by a health care professional to enhance the visual effects of using violet light during the oral exam.

Violet light excites tissue autofluorescence, making pre-cancerous or cancerous tissue appears dark due to its loss of fluorescence. The filtering glasses block the violet excitation light and allow the observation of the tissue's natural fluorescence.

Amber light enhances normal tissue's reflectance properties where the clinician may directly observe the difference between normal and abnormal tissue's vasculature. Studies indicate abnormal tissue has a diffuse vasculature, where normal tissue's vasculature is clearly defined.

The oral screening device 10 may also be used by a surgeon to help identify diseased tissue around a clinically apparent lesion. This will improve the clinician's ability to choose biopsy sites and aid in determining the appropriate margin for surgical excision.

In operation for the various possible modes of light emission from the LED unit 205, the power is switched to the desired circuit by rotating the mode select ring 480 until the desired light source group on the LED unit is activated, with the desired light bandwidth being output.

The general procedure for using the oral screening device 10 is as follows:

1. Turn the on/off switch of the oral screening device to on.
2. Turn the selector switch to a first position to activate the device to produce white light.
3. Conduct a thorough oral examination using standard white light (0-700 nm) and record all relevant findings.
4. Turn the selector switch to a second position to activate the device to produce violet light (405±25 nm).
5. Repeat the oral examination using violet light. Normal tissues will generally fluoresce blue/green and abnormal tissue typically appears as an irregular, dark area.
6. If a suspicious area is discovered, reevaluate that area under white light and violet light again. Since inflammation typically appears darker due to the excess blood content in the inflamed tissue, use the back side of the mirror to apply a light pressure to any suspicious tissue to diffuse any blood from the area and then observe the tissue's fluorescence. If the normal blue/green fluorescence returns, then the lesion probably has an inflammatory component.

7. Turn the selector switch to a third position to activate the device to produce amber light (575±25 nm).

8. Repeat the oral examination using amber light. Normal tissue reflects an amber/orange color and abnormal/diseased tissue appears dark. Pay particular attention to any tissue areas exhibiting abnormal fluorescence under violet light excitation. Amber light is absorbed by hemoglobin and provides sufficient reflective detail to provide detail on regarding the vasculature of the tissue and the topography of the tissue. Closely inspect the tissue vasculature; normal tissue has a well defined vasculature Characteristics that increase suspicion of dysplasia and/or oral cancer include: a highly darkened appearance—strong loss of fluorescence and reflectance, suspicious tissue in a high-risk location (e.g., lateral/ventral tongue), a unilateral presentation of suspicious tissue, asymmetry and/or an irregular shape of the suspected tissue, an extension of the suspected area over more than one kind of oral tissue.

If a suspicious area cannot be ruled out as benign, it is recommended to perform a follow-up examination (typically in 2 weeks) to evaluate whether the suspicious area has changed.

It should be appreciated by those skilled in the art that the conception and the specific embodiment disclosed might be readily utilized as a basis for modifying or redesigning the medical examination device for carrying out the same purposes as the invention. It should be realized by those skilled in the art that such equivalent constructions do not depart from the spirit and scope of the invention as set forth in the appended claims.

What is claimed is:

1. An oral device to screen for precancerous and cancerous tissue comprises:
   (a) a power housing containing a power supply positioned at a first end of the oral device;
   (b) an electronic housing has a proximal end and a distal end, the distal end forms a second end of the oral device, wherein the electronic housing encloses
      (i) a plurality of illumination units, wherein a first illumination unit includes a plurality of light emitters;
      (ii) an electrical system in communication with the plurality of illumination units; and
      (iii) a heat sink, transversing the electronic housing from its proximal end to its distal end, wherein the electrical system is mounted along a length of a planar surface of the heat sink and each illumination unit is separately mounted proximal a distal end of the heat sink and positioned to prohibit emitted light from the plurality of illumination units from mixing before the emitted light exits the oral device and to ensure that the emitted light from the plurality of illumination units illuminate the same area of the oral cavity during screening when the distal end of the electronic housing is inserted into the oral cavity, and wherein the heat sink is in thermal communication with the plurality of illumination units and the electrical system;
   (c) a plurality of emission ports equal to a number of the plurality of illumination units, wherein the plurality of emission ports pierce the electronic housing proximal the distal end of the electronic housing and wherein one emission port is aligned with each illumination unit mounted on the heat sink;
   (d) a number of protective shields equal to a number of the plurality of emission ports, wherein one protective shield is mounted over each emission port; and
   (e) a selector switch mounted on the proximal end of the electronic housing, the selector switch includes a plurality of positions wherein each switch position is wired to activate a predetermined circuit and at least one switch position simultaneously activates more than one light emitter of the first illumination unit.

2. The oral device of claim 1, wherein the first illumination unit includes one light emitter that emits red light, one light emitter that emits blue light, and one light emitter that emits green light.

3. The oral device of claim 1, wherein a first position of the selector switch activates the first illumination unit to emit white light, a second position of the selector switch activates the first illumination unit to emit amber light, and a third position of the selector switch activates a second illumination unit to emit violet light.

4. The oral device of claim 1, further comprises a selectably attachable transparent sheath that fits over a distal end of the electronic housing, wherein whenever the selectably attachable transparent sheath is attached to the oral device the selectably attachable transparent sheath covers all of the plurality of emission ports and the protective shields.

5. The oral device of claim 1, wherein the electrical system includes a microprocessor.

6. The oral device of claim 5, wherein the heat sink includes a thermostat in communication with the microprocessor, the plurality of illumination units, and the selector switch.

7. The oral device of claim 1, further comprises a head mounted lens that has two sections where each section has a different optical characteristic.

8. The oral device of claim 1, further comprises a head mounted lens that contains a long pass filter that passes light that has a wavelength of 435 nm or more.

9. The oral device of claim 1, wherein the heat sink includes various protrusions in thermal communication with the electronic housing.

10. The oral device of claim 1, wherein the first illumination unit includes one light emitter that emits red light, one light emitter that emits blue light, and one light emitter that emits green light and a second illumination unit that has a single light emitter that emits violet light.

11. The oral device of claim 10 that has a first emission port aligned with the first illumination unit and sealed with a first protective shield that is an optical mixing element and a second emission port aligned with the second illumination unit and sealed with a second protective shield that is an optical filter.

12. An oral device to screen for precancerous and cancerous tissue, the oral device comprises:
   (a) a power housing contains a power supply positioned at a first end of the oral device;
   (b) an electronic housing has a proximal end and a distal end, the distal end forms a second end of the oral device, wherein the electronic housing encloses
      (i) a heat sink traversing a longitudinal axis of the electronic housing;
      (ii) a plurality of illumination units, each illumination unit separately mounted proximal a distal end of the heat sink and positioned to prohibit light emitted from the plurality of illumination units from mixing before the emitted light exits the oral device and to ensure that the emitted light from the plurality of illumination units illuminate the same area of the oral cavity during screening when the distal end of the electronic housing is inserted into the oral cavity, wherein a first illumination unit includes a red emitting LED, a green emitting LED and a blue emitting LED and a second illumination unit has a single light emitter;

(iii) an electrical system integrally mounted on a length of a planar surface of the heat sink, the electrical system that has a microprocessor in communication with the plurality of illumination units and the heat sink; and (iv) a thermostat in communication with the heat sink, the plurality of illumination units, and the microprocessor;

(c) a plurality of emission ports equal to a number of the plurality of illumination units, wherein the plurality of emission ports pierce the electronic housing proximal the distal end of the electronic housing and wherein one emission port is aligned with each illumination unit mounted on the heat sink;

(d) a number of protective shields equal to a number of the plurality of emission ports, wherein one protective shield is mounted over each emission port and wherein a first protective shield mounted over a first emission port aligned with the first illumination unit has optical mixing or beam shaping;

(e) a selector switch mounted on the proximal end of the electronic housing, the selector switch includes a plurality of positions wherein each switch position is wired to activate a predetermined circuit and at least one switch position simultaneously activates the red emitting LED, the green emitting LED and the blue emitting LED, of the first illumination unit, and wherein the selector switch is in communication with the microprocessor, the heat sink, and the thermostat.

13. The oral device of claim 12 further comprises a selectably attachable optically transparent sheath that covers the distal end of the electronic housing and all of emission ports when the selectably attachable optically transparent sheath is attached to the oral device.

14. The oral device of claim 13, wherein a first position of the selector switch activates the first illumination unit to emit white light, a second position of the selector switch activates the first illumination unit to emit amber light, and a third position of the selector switch activates the second illumination unit to emit violet light.

15. The oral device of claim 12, further comprises an operator head mounted lens.

16. The oral device of claim 15, wherein the operator head mounted lens contains a long pass filter that passes light having a wavelength of 435 nm or more.

17. The oral device of claim 15, wherein the operator head mounted lens include two sections with each section having a different optical characteristic.

18. The oral device of claim 12 having a second emission port aligned with the second illumination unit and sealed with a second protective shield that is an optical filter.

19. The oral device of claim 18, wherein first illumination unit and second illumination unit are mounted on the heat sink at an incline in relation to the longitudinal axis of the electronic housing.

20. The oral device of claim 19, wherein an intermediate shoulder separates a mounted first illumination unit and a mounted second illumination unit and the first emission port and the second emission port to prohibit the light emitted from the first illumination unit from passing through the second protective shield.

21. The oral device of claim 12, wherein the power housing is mounted on a proximal end of the selector switch and is thermally isolated from the heat sink.

22. The oral device of claim 12, wherein the heat sink includes various protrusions in thermal communication with the electronic housing to dissipate heat through the electronic housing.

23. An oral device to screen an oral cavity for precancerous and cancerous tissue, the oral device comprises:

(a) an electronic housing positioned at a second end of the oral device, the electronic housing has a proximal end and a distal end, wherein the distal end of the electronic housing is inserted into the oral cavity during screening;

(b) a heat sink enclosed by and traversing the electronic housing from the proximal end to the distal end along a longitudinal axis of the electronic housing, wherein the heat sink includes various protrusions in thermal communication with the electronic housing to dissipate heat from a plurality of illumination units through the electric housing;

(c) a first illumination unit includes a plurality of light emitters and a second illumination unit has a single light emitter, wherein the first illumination unit and the second illumination unit are separately mounted approximately parallel to each other on the heat sink proximal the distal end of the electronic housing and are inclined relative to the longitudinal axis of the heat sink, and wherein the first illumination unit and the second illumination unit are positioned to prohibit light emitted from the first illumination unit and the second illumination unit from mixing before the light exits the oral device and to ensure that the light from the first illumination unit and the second illumination unit illuminate the same area of the oral cavity during screening when the distal end of the electronic housing is inserted into the oral cavity;

(d) an electrical system integrally mounted along a length of a planar surface of the heat sink, wherein the electrical system includes a microprocessor in communication with the plurality of illumination units and the heat sink;

(e) a thermostat mounted on the heat sink, wherein the thermostat is in communication with the heat sink, the microprocessor, and the plurality of illumination units;

(f) a first emission port pierces the electronic housing in alignment with the first illumination unit, wherein the first emission port is sealed with a first protective cover, and a second emission port pierces the electronic housing in alignment with the second illumination unit, wherein the second emission port is sealed with a second protective cover;

(g) a selector switch mounted on the proximal end of the electronic housing and in communication with a power supply, the microprocessor and the heat sink, wherein the selector switch includes a plurality of positions with each switch position wired to activate a predetermined circuit to produce a selected wavelength band of light and at least one switch position is wired to simultaneously activate more than one light emitter on the first illumination unit; and (h) a handle, wherein the handle is mounted on a proximal end of the selector switch and is thermally isolated from the heat sink.

24. The oral device of claim 23, wherein the first illumination unit includes light emitters that emit white light, amber light, red light, blue light, and green light.

25. The oral device of claim 23, wherein a first position of the selector switch activates the first illumination unit to emit white light, a second position of the selector switch activates the first illumination unit to emit amber light, and a third position of the selector switch activates the second illumination unit to emit violet light.

26. The oral device of claim 23, further comprises a viewing lens having a long pass filter that passes light that has a wavelength of 435 nm or more.

27. The oral device of claim 23, wherein the viewing lens has two sections where each section has a different optical characteristic.

28. The oral device of claim 23, wherein the plurality of light emitters of the first illumination unit are LED emitters.

29. The oral device of claim 23, wherein at least one illumination unit includes a laser diode.

30. The oral device of claim 23, wherein the first protective cover has optical mixing qualities.

31. The oral device of claim 23, wherein the first protective cover has beam shaping qualities.

32. The oral device of claim 23, wherein the second protective cover is a short pass filter.

* * * * *